(12) United States Patent
Burgess et al.

(10) Patent No.: US 9,221,799 B2
(45) Date of Patent: *Dec. 29, 2015

(54) ANTI-CANCER AGENTS

(71) Applicant: The Walter and Eliza Hall Institute of Medical Research, Parkville, Victoria (AU)

(72) Inventors: Antony Wilks Burgess, Camberwell (AU); Francesca Walker, West Brunswick (AU); Keith Geoffrey Watson, Surrey Hills (AU); Helen Witchard, Engadine (AU); Guillaume Lessene, Coburg (AU)

(73) Assignee: The Walter and Eliza Hall Institute of Medical Research, Parkville (AU)

( * ) Notice: Subject to any disclaimer, the term of this patent is extended or adjusted under 35 U.S.C. 154(b) by 0 days.

This patent is subject to a terminal disclaimer.

(21) Appl. No.: 14/453,502

(22) Filed: Aug. 6, 2014

(65) Prior Publication Data

US 2015/0045365 A1     Feb. 12, 2015

Related U.S. Application Data

(63) Continuation of application No. 13/878,557, filed as application No. PCT/AU2011/001376 on Oct. 27, 2011, now Pat. No. 8,835,629.

(60) Provisional application No. 61/407,265, filed on Oct. 27, 2010.

(51) Int. Cl.
| | |
|---|---|
| C07D 403/12 | (2006.01) |
| A61K 31/53 | (2006.01) |
| A61P 35/00 | (2006.01) |

(52) U.S. Cl.
CPC .............. *C07D 403/12* (2013.01); *A61K 31/53* (2013.01)

(58) Field of Classification Search
CPC ............................. C07D 403/12; A61K 31/53
USPC .......... 544/194, 198, 212, 113, 131; 513/245, 513/231.5; 514/245, 231.5
See application file for complete search history.

(56) References Cited

U.S. PATENT DOCUMENTS

| | | | |
|---|---|---|---|
| 2,742,466 A | 4/1956 | Randall | |
| 3,145,203 A | 8/1964 | Herbert et al. | |
| 4,514,398 A | 4/1985 | Regnier et al. | |
| 4,844,731 A | 7/1989 | Takematsu et al. | |
| 4,932,998 A | 6/1990 | Takematsu et al. | |
| 5,187,045 A | 2/1993 | Bonham et al. | |
| 5,290,754 A | 3/1994 | Nishii et al. | |
| 5,489,591 A | 2/1996 | Kobayashi et al. | |
| 5,536,722 A | 7/1996 | Coe et al. | |
| 5,574,057 A | 11/1996 | Ireland et al. | |
| 5,882,632 A | 3/1999 | Allard et al. | |
| 5,882,633 A | 3/1999 | Pisson et al. | |
| 6,150,360 A | 11/2000 | Daeyaert et al. | |
| 6,262,053 B1 | 7/2001 | Uckun et al. | |
| 6,566,384 B1 | 5/2003 | Owen et al. | |
| 6,774,235 B2 | 8/2004 | Daeyaert et al. | |
| 2004/0122009 A1 | 6/2004 | Chang et al. | |

FOREIGN PATENT DOCUMENTS

| | | |
|---|---|---|
| GB | 1035771 | 11/1962 |
| JP | 52077163 | 12/1975 |
| JP | 62192474 | 8/1987 |
| WO | WO 02059083 | 8/2002 |
| WO | WO 2004026844 | 4/2004 |

OTHER PUBLICATIONS

Aberle, et al., (2007) "Synthesis and biological evaluation of analogues of the anti-tumor alkaloid naamidine A", Bioorganic & Medicinal Chemistry Letters, 17:3741-3744.

Alexander J. Bridges, (2001)"Chemical Inhibitors of Protein Kinases", Chem. Rev., 101:2541-2571.

Backes, W. L.; (2001) "Prodrugs", Clinical Journal of Oncology Nursing, 5(1).

Banker, et al., (1996) "Modern Pharmaceutics" 3ed, Marcel Dekker, New York., pp. 451 and 596.

Bennet & Plum (1996), Cecil Textbook of Medicine, 20th edition, 1:1004-1010.

Bruhin at al., (1969) "Antituberculosis Activity of Some Nitrofuran Derivatives", Journal of pharmacy and pharmacology, 21(7):423-33.

Chan et al. (2012) "Mitosis-targeted anti-cancer therapies: where they stand." Cell Death Disease 3:e411.

Copp, B. R., et al., (1998) "*Naamidine A is an Antagonist of the Epidermal Growth Factor Receptor and an in Vivo Active Antitumor Agent*" J. Med. Chem., 41(20):3909-3911.

Dermer et al., (1994) "Another Anniversary for the War on Cancer", Bio/Technology, 12:320.

Desai et al. (1984) "Preparation of Some 2-(arylamino)-4-[3-(2-methylphenyl)thiazolidine-2,4-dione-5-yl-amino]-6-isonicotinyl hydrazine-S-triazine as Antibacterial and Antituberculostatic Agents" *J Inst Chemists* 56(3):137-139.

(Continued)

*Primary Examiner* — Venkataraman Balasubramanian
(74) *Attorney, Agent, or Firm* — Carol L. Francis; Bozicevic, Field & Francis LLP

(57) ABSTRACT

The present invention provides a compound of Formula (I), or a pharmaceutical acceptable derivative, salt or prodrug thereof. Further provided is a method of treatment of cancer in a subject comprising administering to said subject an effective amount of a compound of Formula (I), or a pharmaceutical acceptable derivative, salt or prodrug thereof. Further provided is the use of a compound of Formula (I), or a pharmaceutical acceptable derivative, salt or prodrug thereof in the preparation of a medicament for the treatment of cancer. In addition, the present invention also provides a pharmaceutical composition comprising a compound of Formula (I), or a pharmaceutical acceptable derivative, salt or prodrug thereof.

16 Claims, 11 Drawing Sheets

(56) References Cited

OTHER PUBLICATIONS

Domingo-Santanes, (2011) "Switches and latches: a biochemical tug-of-war between the kinases and phosphatases that control mitosis" Phil. Trans. R. Soc. B, 366:3584-3594.
Fabbro et al., (2002) "Protein kinases as targets for anticancer agents: from inhibitors to useful drugs" Pharmacology & therapeutics 93, 79-98.
Freshney et ai.,Culture of Animal Cells, A Manual of Basic Technique, Alan R. Liss, Inc., 1983, New York, p. 4.
Golub et al. (1999) "Molecular classification of cancer: class discovery and class prediction by gene expression monitoring" *Science* 286:531-537.
Herman et al., (1990) "Interaction of SR-4233 with Hyperthermia and Radiation in the FSaIIC Murine Fibrosarcoma Tumor System in Vitro and in Vivo", Cancer Research 50, pp. 5055-5059.
Honda et al., (1984) "Oxidative Replacement of the Hydrazino Group by Hydrogen in Hydrazono-1,3,5-triazines.II. Synthesis of 2,4-(substituted diamino)-1,3,5-triazines by oxidation of 2,4-(substituted diamino)-6-hydrazino-1,3,5-triazines", Fukui Daigaku Kōgakubu kenkyū hōkoku (Memoirs of the Graduate School of Engineering, University of Fukui), 32(2):239-50.
Krystof et al. (2012) "Perspective of cyclin-dependent kinase 9 (CDK9) as a drug target" *Current Pharmaceutical Design*, 18: 2883-2890.
Mass, R. D., (2004) "The HER receptor family: a rich target for therapeutic development" Int. J. Radiation Oncology Bio. Phys.vol. 58(3): 932-940.
McCormick et al., (1981) "Biodegradation of Hexahydro-1,3,5-trinitro-1,3,5-triazine", Applied and Environmental Microbiology, pp. 817-823.
Modha J.; Datta, N.; Parekh H.; (2001) "Synthesis and Biological Evaluation of Some New 3,4-dihydropyrimidin-4-ones", Farmaco 56(9):641-646.
Moon , H. S., et al., (2002) "A Novel Microtubule Destabilizing Entity from Orthogonal Synthesis of Triazine Library and Zebrafish Embryo Screening" *J. Am. Chem. Soc.*, 124(39):11608-11609.
Shukla et al., (1982) "Studies on Anti-tubercular agents: Preparation of some 2-(arylamino)-4-[α-(2-hydroxy-1-naphthyl) benzylamino]-6-(isonicotinoylhydrazino)-1,3,5-triazines", Journal of the Institution of Chemists, 54(3):130-2.
Witchard & Watson (2010) "Synthesis of 5-amino-3-methylimidazolidine-2,4-dione and 1,3,5-triazine Derivatives as analogues of the Alkaloids Naamidine A and G" *Synthesis* (24):4312-4316.
Wolff Manfred E. "Burger's Medicinal Chemistry, 5ed, Part 1" John Wiley & Sons, 1995, pp. 975-977.
Yaguchi, et al., (1997) "In Vitro Cytotoxicity of Imidazlyl-1,3,5,-triazine Derivatives", Biol. Pharm. Bull. 20(6) 698-700.
Yamase et al., (1964) "Reactive Dyes Containing Hydrazine Groups", Kogyo Kagaku Zasshi (Journal of the Chemical Society of Japan), 67(1): 106-10.

ANTI-CANCER AGENTS

FIELD OF THE INVENTION

The present invention relates to a class of compounds useful in the treatment of cancer, such as colon cancer, lung cancer, brain cancer and breast cancer.

BACKGROUND OF THE INVENTION

Cancer is a major disease that is a leading cause of death worldwide. A major aspect of the treatment of cancer is chemotherapy using anti-cancer agents. However, the treatment of cancer using chemotherapy is rarely straightforward and there is a general need to develop new and improved anti-cancer agents which act by different mechanisms and pathways.

SUMMARY OF THE INVENTION

In a first aspect, the present invention provides a compound of Formula I, or a pharmaceutical acceptable derivative, salt or prodrug thereof, wherein:

Formula I

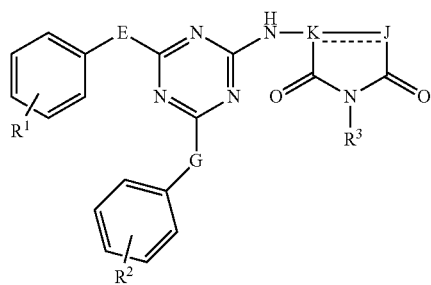

E and G are each independently selected from the group consisting of $-C_{1-4}$alkyl-, $-NH-$, $-N(C_{1-4}$alkyl$)-$, $-O-$ and, in either orientation, $-NH-C_{1-4}$alkyl-, $-N(C_{1-4}$alkyl$)-C_{1-4}$alkyl-, and $-O-C_{1-4}$alkyl-; and
$====$ is a single or double bond;
  when $====$ is a single bond, K is independently selected from CH and N, and J is independently selected from NH and $CH_2$; or
  when $====$ is a double bond, K is C, and J is independently selected from N and CH;
$R^1$ is 0-2 substituents wherein each substituent is independently selected from the group consisting of $-C_{1-4}$alkyl, $-C_{3-6}$cycloalkyl, $-OH$, $-O-C_{1-4}$alkyl, $-N(R^4)_2$, $-C_{1-4}$alkylN$(R^4)_2$, $-O-C_{1-4}$alkyl-N$(R^4)_2$, $-C_{3-6}$cycloalkyl-N$(R^4)_2$, $-O$-phenyl, $-O$-benzyl, $-NO_2$, halogen, and $CF_3$;
  each $R^4$ is independently selected from the group consisting of $-H$, $-OH$, $-C_{1-4}$alkyl, $-C(O)OC_{1-4}$alkyl, $-C_{1-4}$alkyl-OR$^7$, and $-C(O)R^5$, provided that if one $R^4$ is $-OH$ then the other $R^4$ cannot be $-OH$; or
  $-N(R^4)_2$ forms a pyrrolidinyl, piperidinyl, piperazinyl, or morpholino group optionally substituted with $-C_{1-4}$alkyl;
$R^2$ is 0-2 substituents wherein each substituent is independently selected from the group consisting of $-C_{1-4}$alkyl, $-C_{3-6}$cycloalkyl, $-OH$, $-O-C_{1-4}$alkyl, $-N(R^6)_2$, $-C_{1-4}$alkylN$(R^6)_2$, $-O-C_{1-4}$alkyl-N$(R^6)_2$, $-C_{3-6}$cycloalkyl-N$(R^6)_2$, $-O$-phenyl, $-O$-benzyl, $-NO_2$, halogen, and $-CF_3$;

each $R^6$ is independently selected from the group consisting of $-H$, $-OH$, $-C_{1-4}$alkyl, $-C(O)OC_{1-4}$alkyl, $-C_{1-4}$alkyl-OR$^7$, and $-C(O)R^8$, provided that if one $R^6$ is $-OH$ then the other $R^6$ cannot be $-OH$; or
$-N(R^6)_2$ forms a pyrrolidinyl, piperidinyl, piperazinyl, or morpholino group optionally substituted with $-C_{1-4}$alkyl;
wherein each of $R^5$ and $R^8$ are independently selected from the group consisting of $-C_{1-4}$alkyl and -phenyl;
$R^3$ is selected from the group consisting of H, $-C_{1-4}$alkyl, aryl, and alkylaryl; and
wherein $R^7$ is selected from the group consisting of $-H$ and $-C_{1-4}$alkyl.

In a second aspect, the present invention provides a method of treatment of cancer in a subject comprising administering to said subject an effective amount of a compound of the present invention or a pharmaceutically acceptable derivative, salt or prodrug thereof.

In a third aspect, the present invention provides the use of a compound of the present invention or a pharmaceutically acceptable derivative, salt or prodrug thereof in the preparation of a medicament for the treatment of cancer.

In a fourth aspect, the present invention provides a pharmaceutical composition comprising a compound of the present invention or a pharmaceutically acceptable derivative, salt or prodrug thereof and a pharmaceutically acceptable carrier, diluent or excipient.

DETAILED DESCRIPTION OF THE INVENTION

Figure 1:
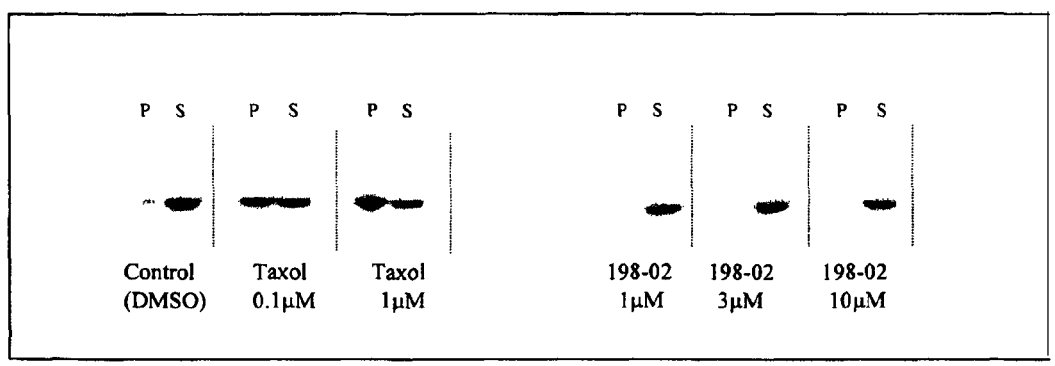
FIG. 1: Determination of stabilized vs soluble tubulin in cells treated with G2/M blockers. LIM1215 cells treated with vehicle, Taxol or compound 3 (198-02) were solubilized in NP-40. Equal volumes of supernatant and resuspended insoluble material were analyzed by SDS/PAGE and immunoblotting with antibodies to β-tubulin. S=soluble and P=polymerized tubulin. Similar results were obtained on the BaF/3 cell line.

Naamidine A, an imidazole alkaloid extracted from *Leucetta* sponges, has been reported to selectively inhibit the epidermal growth factor (EGF) signalling pathway and to inhibit tumour growth in a mouse xenograft model using a human cancer cell line that greatly over expresses the EGF receptor (Copp et al., J. Med. Chem. 1998, 41:3909).

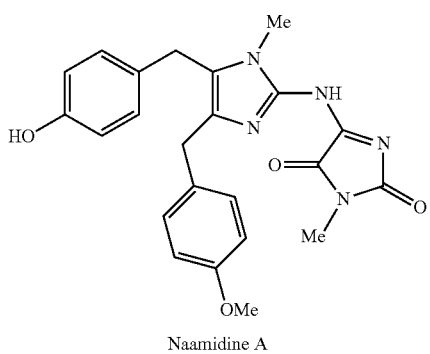 [SMILES: COc1ccc(Cc2nc(NC3=NC(=O)N(C)C3=O)n(C)c2Cc2ccc(O)cc2)cc1]

Naamidine A

In a search for EGF-receptor-specific small molecules inhibitors, the present inventors synthesised a number of Naamidine A analogues and assessed their biological activity.

Surprisingly, the present inventors identified a class of molecules related to Naamidine A that show cytostatic and/or cytotoxic activity and which do not act through the EGF signalling pathway. This class of triazine compounds show promise as anti-cancer agents with anticancer activity in the nanomolar range.

Accordingly, in a first aspect, the present invention provides a compound of formula I, or a pharmaceutical acceptable derivative, salt or prodrug thereof, wherein:

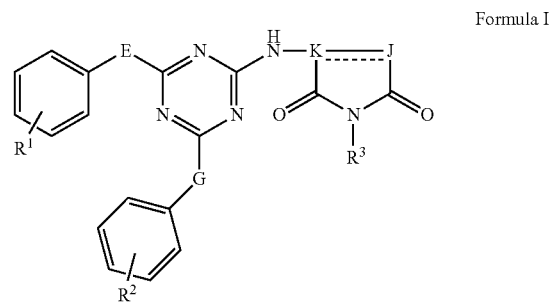

Formula I

E and G are each independently selected from the group consisting of —$C_{1-4}$alkyl-, —NH—, —N($C_{1-4}$alkyl)-, —O— and, in either orientation, —NH—$C_{1-4}$alkyl-, —N($C_{1-4}$alkyl)-$C_{1-4}$alkyl-, and —O—$C_{1-4}$alkyl-; and ---- is a single or double bond;

when ---- is a single bond, K is independently selected from CH and N, and is independently selected from NH and $CH_2$; or when ---- is a double bond, K is C, and J is independently selected from N and CH;

$R^1$ is 0-2 substituents (meaning 0, 1, or 2 substituents or a range comprising any of two of those integers) wherein each substituent is independently selected from the group consisting of —$C_{1-4}$alkyl, —$C_{3-6}$cycloalkyl, —OH, —O—$C_{1-4}$alkyl, —N($R^4$)$_2$, —$C_{1-4}$alkylN($R^4$)$_2$, —O—$C_{1-4}$alkyl-N($R^4$)$_2$, —$C_{3-6}$cycloalkyl-N($R^4$)$_2$, —O-phenyl, —O-benzyl, —$NO_2$, halogen, and —$CF_3$;

each $R^4$ is independently selected from the group consisting of —H, —OH, —C(O)O$C_{1-4}$alkyl, —$C_{1-4}$alkyl-O$R^7$, and —C(O)$R^5$, provided that if one $R^4$ is —OH then the other $R^4$ cannot be —OH; or —N($R^4$)$_2$ forms a pyrrolidinyl, piperidinyl, piperazinyl, or morpholino group optionally substituted with —$C_{1-4}$alkyl;

$R^2$ is 0-2 substituents (meaning 0, 1, or 2 substituents or a range comprising any of two of those integers) wherein each substituent is independently selected from the group consisting of —$C_{1-4}$alkyl, —$C_{3-6}$cycloalkyl, —OH, —O—$C_{1-4}$alkyl, —N($R^6$)$_2$, —$C_{1-4}$alkylN($R^6$)$_2$, —O—$C_{1-4}$alkyl-N($R^6$)$_2$, —$C_{3-6}$cycloalkyl-N($R^6$)$_2$, —O-phenyl, —O-benzyl, —$NO_2$, halogen, and —$CF_3$;

each $R^6$ is independently selected from the group consisting of —H, —OH, —C(O)O$C_{1-4}$alkyl, —$C_{1-4}$alkyl-O$R^7$, and —C(O)$R^8$, provided that if one $R^6$ is —OH then the other $R^6$ cannot be —OH; or —N($R^6$)$_2$ forms a pyrrolidinyl, piperidinyl, piperazinyl, or morpholino group optionally substituted with —$C_{1-4}$alkyl;

wherein each of $R^5$ and $R^8$ are independently selected from the group consisting of —$C_{1-4}$alkyl and -phenyl;

$R^3$ is selected from the group consisting of H, —$C_{1-4}$alkyl, -aryl, and -alkylaryl; and wherein $R^7$ is selected from the group consisting of —H and —$C_{1-4}$alkyl.

In one embodiment, ---- is a single bond and (i) K is CH and J is NH, or (ii) K is N and J is $CH_2$.

In another embodiment, ---- is a double bond and K is CH and J is NH.

Preferably, $R^3$ is selected from the group consisting of hydrogen, methyl, propyl, butyl, and phenyl.

In one embodiment, E is selected from the group consisting of —NH—$C_{1-4}$alkyl-, —N($C_{1-4}$alkyl)-$C_{1-4}$alkyl-, and —O—$C_{1-4}$alkyl-; wherein the heteroatom of E is bonded to the triazine ring.

In one embodiment, G is selected from the group consisting of —N(C$_{1-4}$alkyl)-C$_{1-4}$alkyl-, and —O—C$_{1-4}$alkyl-; wherein the heteroatom of G is bonded to the triazine ring.

Preferably, E is —NHC$_{1-4}$alkyl, more preferably E is —NH—CH$_2$—.

Preferably, G is —NHC$_{1-4}$alkyl, more preferably G is —NH—CH$_2$—.

In one embodiment where R$^1$ is —N(R$^4$)$_2$ which forms is a piperazinyl group substituted with —C$_{1-4}$alkyl, of the formula:

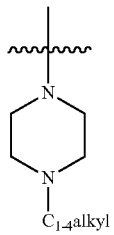

Preferably, R$^1$ and R$^2$ are each independently 1-2 substituents, more preferably R$^1$ and R$^2$ are each 1 substituent.

In one embodiment, each of R$^1$ and R$^2$ is at least one para substituent.

Preferably, each R$^1$ substituent is independently selected from the group consisting of —OH, —O—C$_{1-4}$alkyl, and —C$_{1-4}$alkyl, more preferably, each R$^1$ substituent is independently selected from the group consisting —OH, —OMe, and —CH$_3$.

Preferably, each R$^2$ substituent is independently selected from the group consisting of —OH, O—C$_{1-4}$alkyl, and —C$_{1-4}$alkylN(R$^6$)$_2$.

More preferably, each R$^2$ substituent is independently selected from the group consisting of —OH, —OMe, —CH$_2$NH$_2$, and —CH$_2$NH—C(O)O(t-Bu).

In a preferred embodiment, the present invention provides a compound of Formula II or a pharmaceutical derivative, salt or prodrug thereof, wherein:

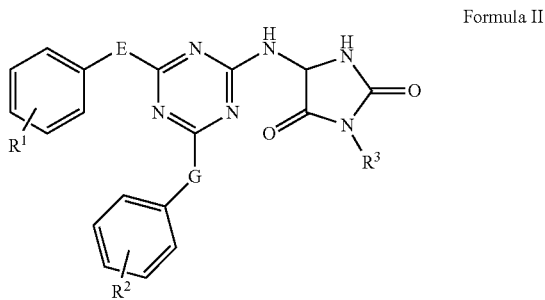

Formula II

E and G are each independently selected from the group consisting of —C$_{1-4}$alkyl-, —NH—, —O— and, in either orientation —NH—C$_{1-4}$alkyl-, and —O—C$_{1-4}$alkyl-; and R$^1$ is 0-2 substituents wherein each substituent is independently selected from the group consisting of —C$_{1-4}$alkyl, —C$_{3-6}$cycloalkyl, —OH, —O—C$_{1-4}$alkyl, —N(R$^4$)$_2$, —C$_{1-4}$alkylN(R$^4$)$_2$, —O—C$_{1-4}$alkyl-N(R$^4$)$_2$, —C$_{3-6}$cycloalkyl-N(R$^4$)$_2$, —O-phenyl, —O-benzyl, —NO$_2$, halogen, and —CF$_3$;

each R$^4$ is independently selected from the group consisting of —H, —OH, —C$_{1-4}$alkyl, —C(O)OC$_{1-4}$alkyl, —C$_{1-4}$alkyl-OR$^7$, and —C(O)R$^5$, provided that if one R$^4$ is —OH then the other R$^4$ cannot be —OH; or
—N(R$^4$)$_2$ forms a pyrrolidinyl, piperidinyl, piperazinyl, or morpholino group optionally substituted with —C$_{1-4}$alkyl;

R$^2$ is 0-2 substituents wherein each substituent is independently selected from the group consisting of —C$_{1-4}$alkyl, —C$_{3-6}$cycloalkyl, —OH, —O—C$_{1-4}$ alkyl, —N(R$^6$)$_2$, —C$_{1-4}$alkylN(R$^6$)$_2$, —O—C$_{1-4}$alkyl-N(R$^6$)$_2$, —C$_{3-6}$cycloalkyl-N(R$^6$)$_2$, —O-phenyl, —O-benzyl, —NO$_2$, halogen, and —CF$_3$;

each R$^6$ is independently selected from the group consisting of —H, —OH, —C$_{1-4}$alkyl, —C(O)OC$_{1-4}$alkyl, —C$_{1-4}$alkyl-OR$^7$, and —C(O)R$^8$, provided that if one R$^6$ is —OH then the other R$^6$ cannot be —OH; or
—N(R$^6$)$_2$ forms a pyrrolidinyl, piperidinyl, piperazinyl, or morpholino group optionally substituted with —C$_{1-4}$alkyl;

wherein each of R$^5$ and R$^8$ are independently selected from the group consisting of —C$_{1-4}$alkyl and -phenyl;

R$^3$ is selected from the group consisting of —H, —C$_{1-4}$alkyl, and -aryl;

wherein R$^7$ is selected from the group consisting of —H and —C$_{1-4}$alkyl.

In one embodiment, E is selected from the group consisting of —NH—C$_{1-4}$alkyl-, —N(C$_{1-4}$alkyl)-C$_{1-4}$alkyl-, and —O—C$_{1-4}$alkyl-; wherein the heteroatom of B is bonded to the triazine ring.

In one embodiment, G is selected from the group consisting of —NH—C$_{1-4}$alkyl-, —N(C$_{1-4}$alkyl)-C$_{1-4}$alkyl-, and —O—C$_{1-4}$alkyl-; wherein the heteroatom of G is bonded to the triazine ring.

Preferably, E is —NHC$_{1-4}$alkyl, more preferably. E is —NH—CH$_2$—.

Preferably G is —NHC$_{1-4}$alkyl, more preferably, G is —NH—CH$_2$—.

In one embodiment the present invention provides a compound of formula II wherein R$^1$ is 1-2 substituents wherein each substituent is independently selected from the group consisting of —C$_{1-4}$alkyl, —OH, —O—C$_{1-4}$alkyl, and —C$_{1-4}$alkylNHR$^4$; and R$^2$ is 1-2 substituents wherein each substituent is independently selected from the group consisting of —C$_{1-4}$alkyl, —OH, —O—C$_{1-4}$alkyl, and —C$_{1-4}$alkylNHR$^6$ wherein R$^4$ is selected from the group consisting of —H, —C$_{1-4}$alkyl, —C(O)OC$_{1-4}$alkyl;

wherein R$^6$ is selected from the group consisting of —H, —C$_{1-4}$alkyl, —C(O)OC$_{1-4}$alkyl;

Preferably, each R$^1$ substituent is independently selected from the group consisting of —OH, —OMe, —CH$_3$ and each R$^2$ substituent is independently selected from the group consisting of —OH, —O—C$_{1-4}$alkyl, —C$_{1-4}$alkylNHR$^6$;

wherein R$^6$ is selected from the group consisting of —H, —C$_{1-4}$alkyl, and —C(O)OC$_{1-4}$alkyl.

More preferably, R$^2$ is selected from the group consisting of —OH, —OMe, —CH$_2$NH$_2$, and —CHNH—C(O)O(t-Bu).

In another embodiment, the present invention provides a compound of formula II wherein R$^3$ is selected from the group consisting of —H, methyl, propyl, butyl and phenyl.

In one embodiment, R$^3$ is a straight alkyl chain.

In one embodiment, the present invention provides a compound of Formula III or a pharmaceutical derivative, salt or prodrug thereof, wherein:

Formula III

E and G are each independently selected from the group consisting of —C$_{1-4}$alkyl-, —NH—, —O— and, in either orientation, —NH—C$_{1-4}$alkyl-, and —O—C$_{1-4}$alkyl-;

R$^1$ is 0-2 substituents wherein each substituent is independently selected from the group consisting of —C$_{1-4}$alkyl, —C$_{3-6}$cycloalkyl, —OH, —O—C$_{1-4}$alkyl, —N(R$^4$)$_2$, —C$_{1-4}$alkylNHR$^4$, —O—C$_{1-4}$alkyl-N(R$^4$)$_2$, —C$_{3-6}$cycloalkyl-N(R$^4$)$_2$, —O-phenyl, —O-benzyl, —NO$_2$, halogen, and —CF$_3$;

wherein each R$^4$ is independently selected from the group consisting of —H, —OH, C$_{1-4}$alkyl, —C(O)OC$_{1-4}$alkyl, —C$_{1-4}$alkyl-OR$^7$, and —C(O)R$^5$, provided that if one R$^4$ is —OH then the other R$^4$ cannot be —OH; or —N(R$^4$)$_2$ forms a pyrrolidinyl, piperidinyl, piperazinyl, or morpholino group optionally substituted with —C$_{1-4}$alkyl;

R$^2$ is 0-2 substituents wherein each substituent is independently selected from the group consisting of —C$_{1-4}$alkyl, —C$_{3-6}$cycloalkyl, —OH, —O—C$_{1-4}$ alkyl, —N(R$^6$)$_2$, —C$_{1-4}$alkylN(R$^6$)$_2$, —O—C$_{1-4}$alkyl-N(R$^6$)$_2$, —C$_{3-6}$cycloalkyl-N(R$^6$)$_2$, —O-phenyl, —O-benzyl, —NO$_2$, halogen, and —CF$_3$;

each R$^6$ is independently selected from the group consisting of —H, —OH, —C$_{1-4}$alkyl, —C(O)OC$_{1-4}$alkyl, —C$_{1-4}$alkyl-OR$^7$, and —C(O)R$^8$, provided that if one R$^6$ is —OH then the other R$^6$ cannot be —OH; or —N(R$^6$)$_2$ forms a pyrrolidinyl, piperidinyl, piperazinyl, or morpholino group optionally substituted with —C$_{1-4}$alkyl;

wherein each of R$^5$ and R$^8$ are independently selected from the group consisting of —C$_{1-4}$alkyl and -phenyl;

R$^3$ is selected from the group consisting of —H, —C$_{1-4}$alkyl, and -aryl; and wherein R$^7$ is selected from the group consisting of —H and —C$_{1-4}$alkyl.

In one embodiment, E is selected from the group consisting of —NH—C$_{1-4}$alkyl-, —N(C$_{1-4}$alkyl)-C$_{1-4}$alkyl-, and —O—C$_{1-4}$alkyl-; wherein the heteroatom of E is bonded to the triazine ring.

In one embodiment, G is selected from the group consisting of —NH—C$_{1-4}$alkyl-, —N(C$_{1-4}$alkyl)-C$_{1-4}$alkyl-, and —O—C$_{1-4}$alkyl-; wherein the heteroatom of G is bonded to the triazine ring.

Preferably E is —NHC$_{1-4}$alkyl, more preferably E is —NH—CH$_2$—.

Preferably G is —NHC$_{1-4}$alkyl, more preferably G is —NH—CH$_2$—.

In one embodiment the present invention provides a compound of formula III wherein R$^1$ is 1-2 substituents wherein each substituent is independently selected from the group consisting of —O—C$_{1-4}$alkyl, and —C$_{1-4}$alkylN(R$^4$)$_2$; and R$^2$ is 1-2 substituents wherein each substituent is independently selected from the group consisting of —O—C$_{1-4}$alkyl, and —C$_{1-4}$alkylN(R$^6$)$_2$;

wherein each R$^4$ is independently selected from the group consisting of —H, —C(O)OC$_{1-4}$alkyl;

wherein each R$^6$ is independently selected from the group consisting of —H, —C$_{1-4}$alkyl, —C(O)OC$_{1-4}$alkyl;

Preferably, R$^1$ is —OMe and R$^2$ is selected from the group consisting —O—C$_{1-4}$alkyl, and —C$_{1-4}$alkylN(R$^6$)$_2$;

wherein each R$^6$ is independently selected from the group consisting of —H, —C$_{1-4}$alkyl, and —C(O)OC$_{1-4}$alkyl.

More preferably, R$^2$ is selected from the group consisting of —OMe, —CH$_2$NH$_2$, and —CHNH—C(O)O(t-Bu).

Preferably, R$^3$ is hydrogen.

In one embodiment, the present invention provides a compound of Formula IV or a pharmaceutical derivative, salt or prodrug thereof, wherein:

Formula IV

E and G are each independently selected from the group consisting of —C$_{1-4}$alkyl, —NH—, —O— and, in either orientation, —NH—C$_{1-4}$alkyl-, and —O—C$_{1-4}$alkyl-;

R$^1$ is 0-2 substituents wherein each substituent is independently selected from the group consisting of —C$_{1-4}$alkyl, —C$_{3-6}$cycloalkyl, —OH, —O—C$_{1-4}$ alkyl, N(R$^4$)$_2$, —C$_4$alkylNHR$^4$, —O—C$_{1-4}$alkyl-N(R$^4$)$_2$, —O—C$_{1-4}$alkyl-N(R$^4$)$_2$, —C$_{3-6}$cycloalkyl-N(R$^4$)$_2$, —O-phenyl, —O-benzyl, —NO$_2$, halogen, and —CF$_3$;

wherein each R$^4$ is independently selected from the group consisting of —H, C$_{1-4}$alkyl, —C(O)OC$_{1-4}$alkyl, —C$_{1-4}$alkyl-OR$^7$, and —C(O)R$^5$; or —N(R$^4$)$_2$ forms a pyrrolidinyl, piperidinyl, piperazinyl, or morpholino group optionally substituted with —C$_{1-4}$alkyl;

R$^2$ is 0-2 substituents wherein each substituent is independently selected from the group consisting of —C$_{1-4}$alkyl, —C$_{3-6}$cycloalkyl, —OH, —O—C$_{1-4}$ alkyl, N(R$^6$)$_2$, —C$_{1-4}$alkylN(R$^6$)$_2$, —O—C$_{1-4}$alkyl-N(R$^6$)$_2$, —C$_{3-6}$cycloalkyl-N(R$^6$)$_2$, —O-phenyl, —O-benzyl, —NO$_2$, halogen, and —CF$_3$;

each R$^6$ is independently selected from the group consisting of —H, —OH, —C$_{1-4}$alkyl, —C(O)OC$_{1-4}$alkyl, —C$_{1-4}$alkyl-OR$^7$, and —C(O)R$^8$, provided that if one R$^6$ is —OH then the other R$^6$ cannot be —OH; or —N(R$^6$)$_2$ forms a pyrrolidinyl, piperidinyl, piperazinyl, or morpholino group optionally substituted with —C$_{1-4}$alkyl;

wherein each of $R^5$ and $R^8$ are independently selected from the group consisting of —$C_{1-4}$alkyl and -phenyl;

$R^3$ is selected from the group consisting of —H, —$C_{1-4}$alkyl, and -aryl; and wherein $R^7$ is selected from the group consisting of —H and —$C_{1-4}$alkyl.

In one embodiment, E is selected from the group consisting of —NH—$C_{1-4}$alkyl-, —N($C_{1-4}$alkyl)-$C_{1-4}$alkyl-, and —O—$C_{1-4}$alkyl-; wherein the heteroatom of E is bonded to the triazine ring.

In one embodiment, G is selected from the group consisting of —NH—$C_{1-4}$alkyl-, —N($C_{1-4}$alkyl)-$C_{1-4}$alkyl-, and —O—$C_{1-4}$alkyl-; wherein the heteroatom of G is bonded to the triazine ring.

Preferably E is —NH$C_{1-4}$alkyl, more preferably E is —NH—$CH_2$—.

Preferably G is —NH$C_{1-4}$alkyl, more preferably G is —NH—$CH_2$—.

In one embodiment the present invention provides a compound of formula IV wherein $R^1$ is 1-2 substituents wherein each substituent is independently selected from the group consisting of —O—$C_{1-4}$alkyl, and —$C_{1-4}$alkylN($R^4$)$_2$; and $R^2$ is 1-2 substituents wherein each substituent is independently selected from the group consisting of —O—$C_{1-4}$alkyl, and —$C_{1-4}$alkylN($R^6$)$_2$;

wherein each $R^4$ is independently selected from the group consisting of —H, —$C_{1-4}$alkyl, —C(O)O$C_{1-4}$alkyl;

wherein each $R^6$ is independently selected from the group consisting of —H, —$C_{1-4}$alkyl, —C(O)O$C_{1-4}$alkyl;

Preferably, $R^1$ is –OMe and $R^2$ is selected from the group consisting —O—$C_{1-4}$alkyl, and —$C_{1-4}$alkylN($R^6$)$_2$;

wherein each $R^6$ is independently selected from the group consisting of —H, —$C_{1-4}$alkyl, and —C(O)O$C_{1-4}$alkyl.

More preferably, $R^2$ is selected from the group consisting of —OMe, —$CH_2NH_2$, and —CHNH—C(O)O(t-Bu).

In another embodiment, the present invention provides a compound of formula IV wherein $R^3$ is selected from the group consisting of —H, methyl, propyl, butyl and phenyl. Preferably, $R^3$ is hydrogen.

In one embodiment the present invention provides a compound selected from the group consisting of:

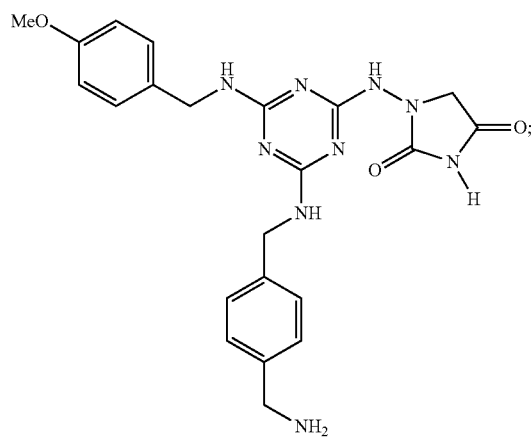

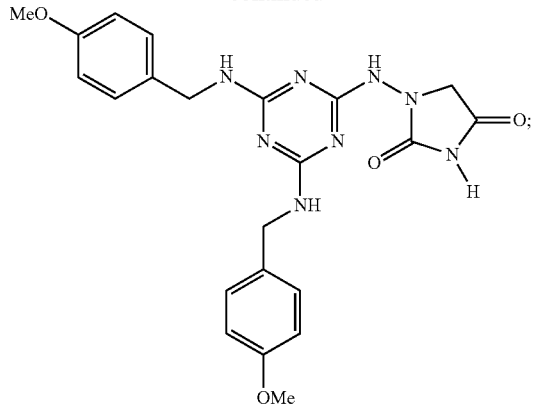

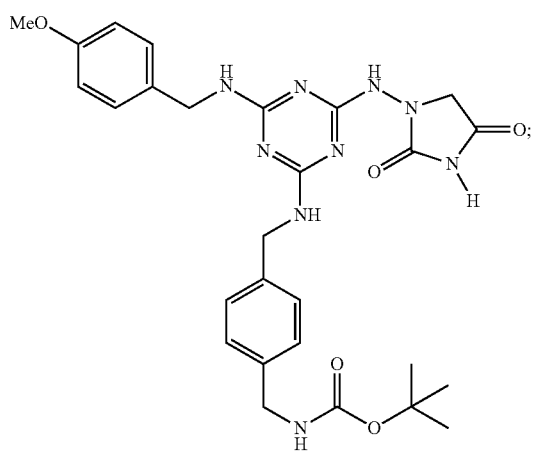

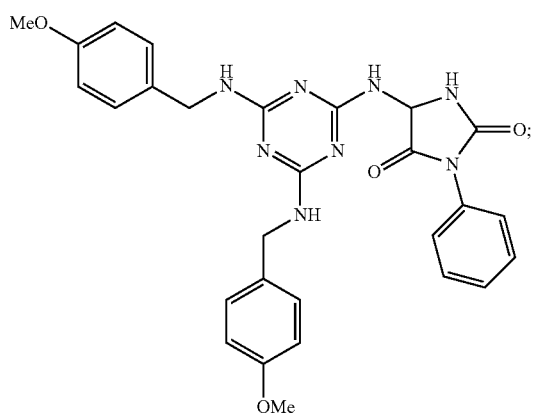

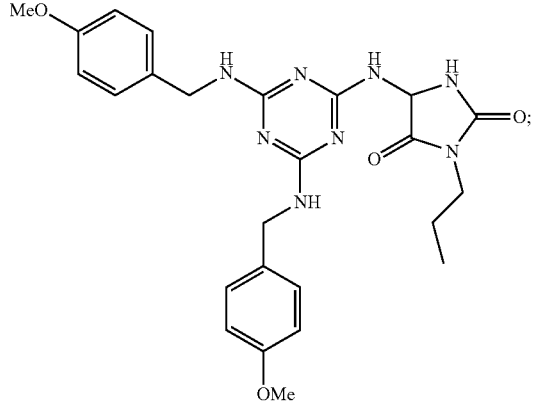

-continued
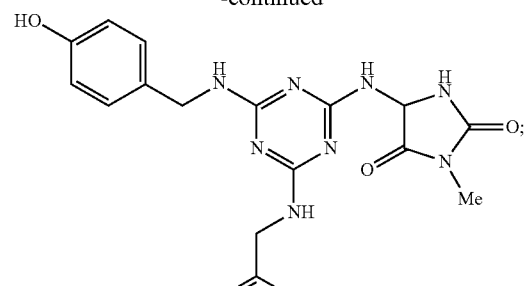
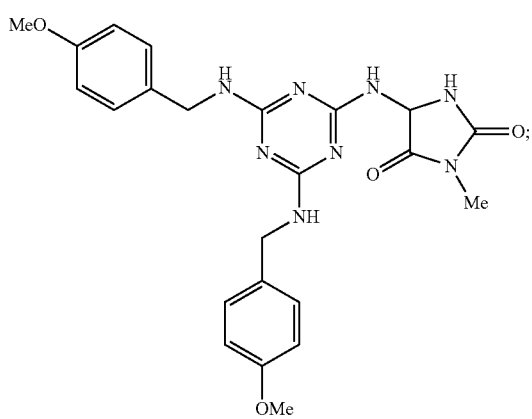
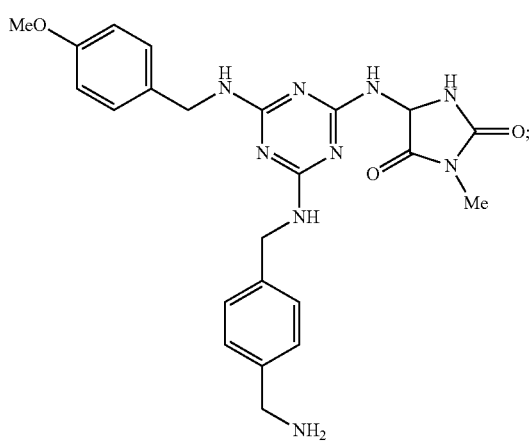
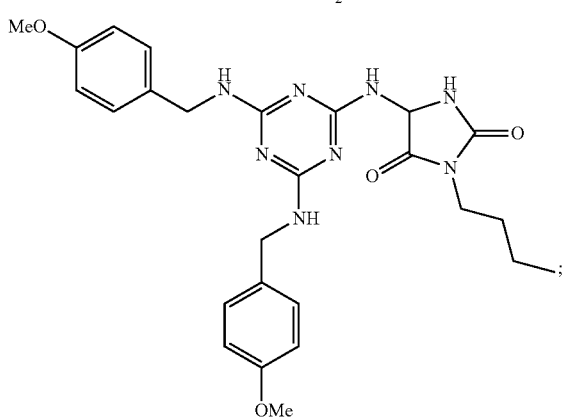
-continued
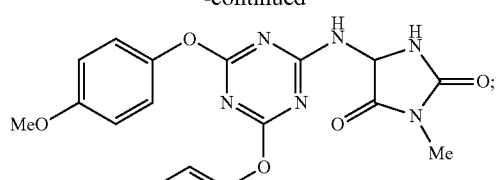
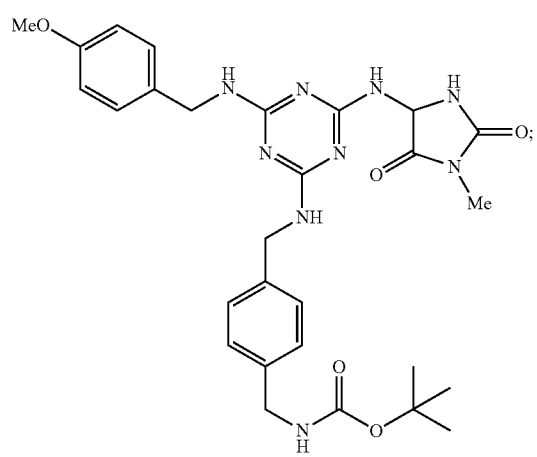
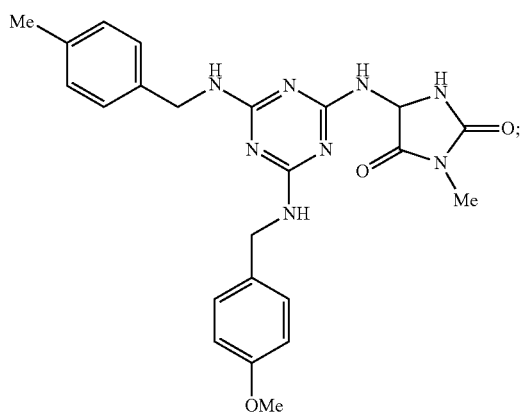
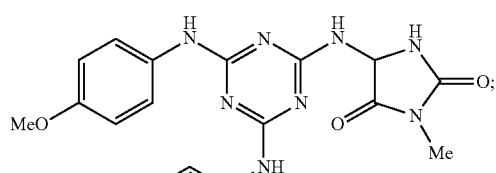
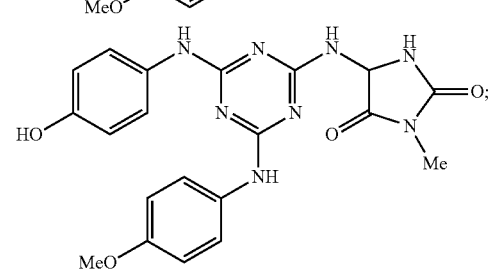

13
-continued
14
-continued
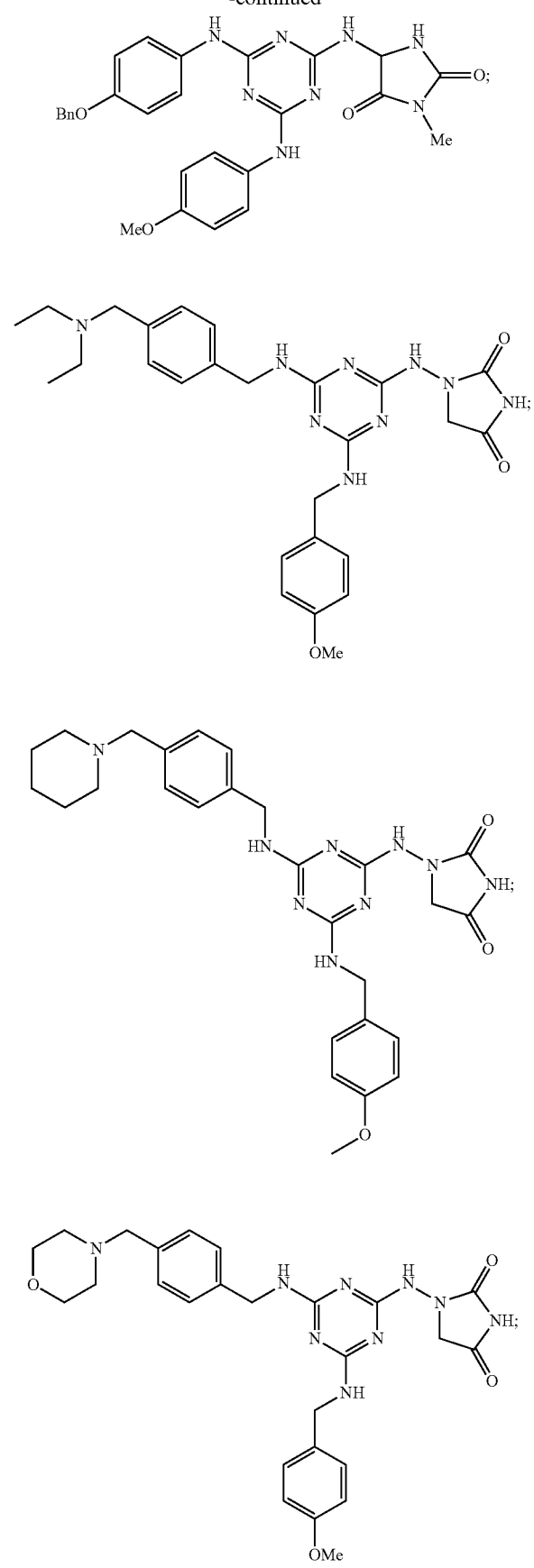
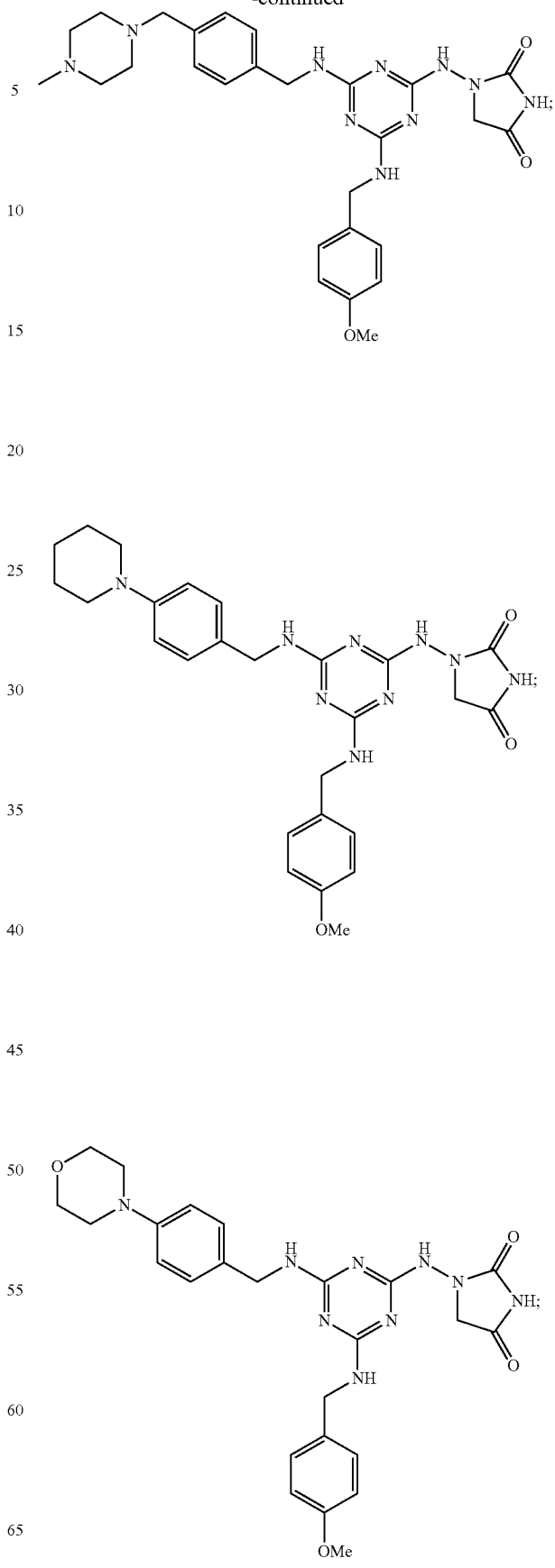

15
-continued
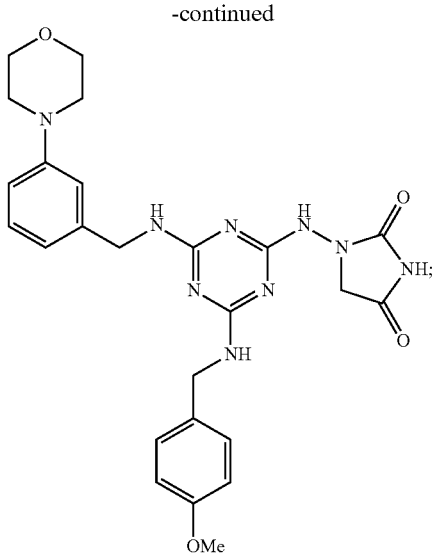
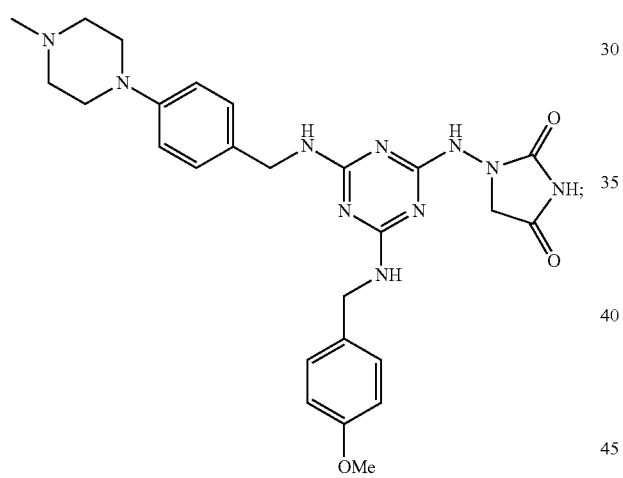
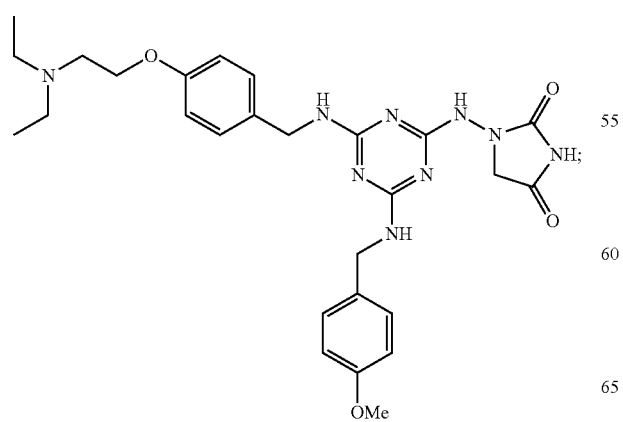
16
-continued
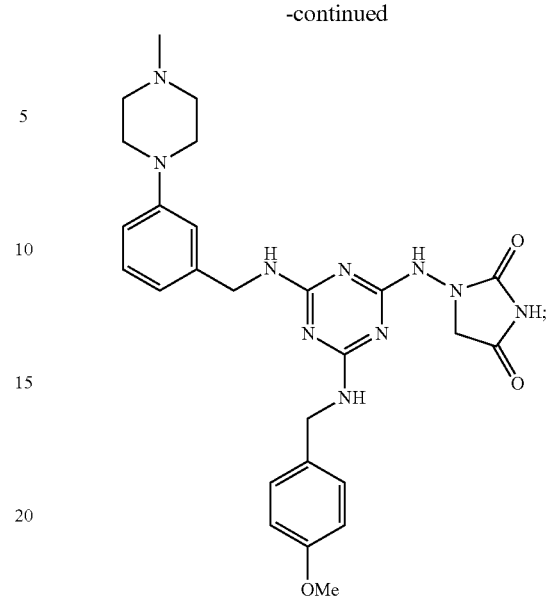
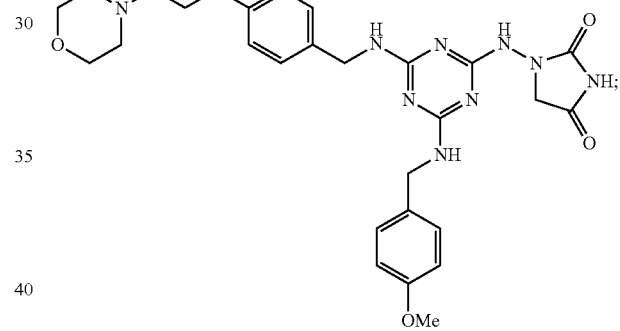
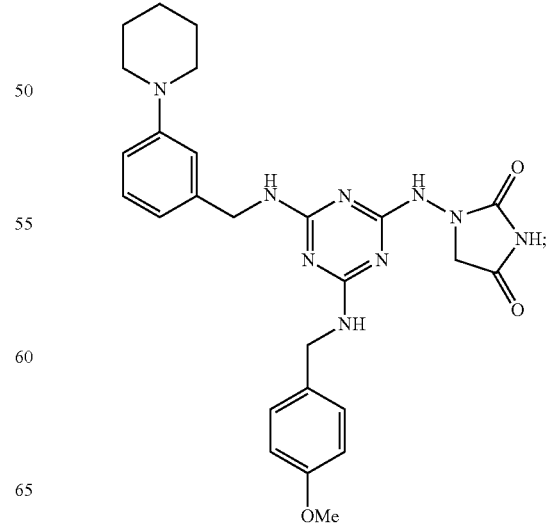

-continued

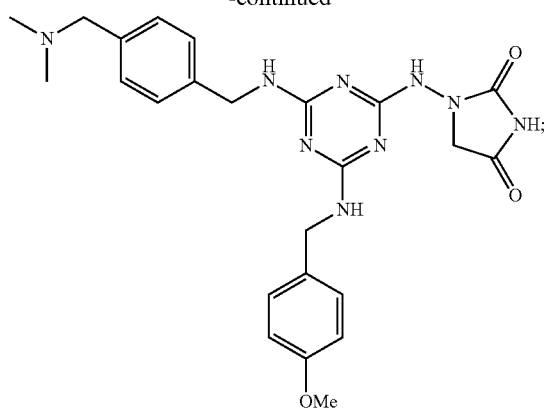

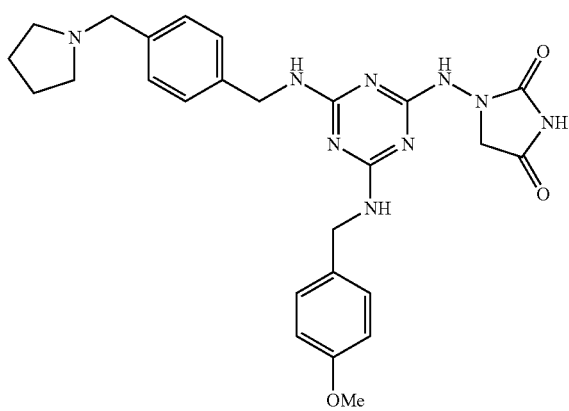

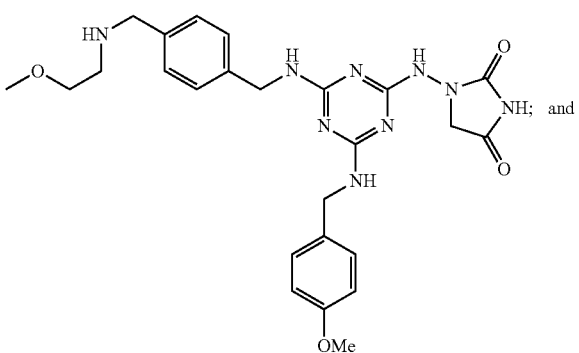

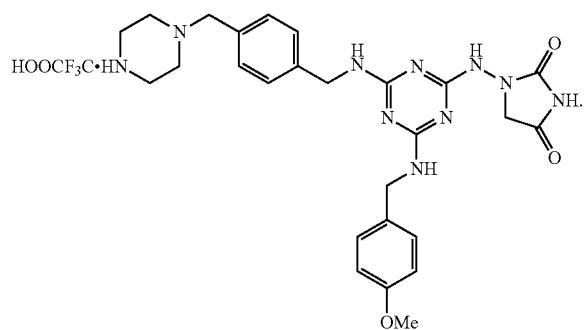

Preferably, the compound is selected from the group consisting of:

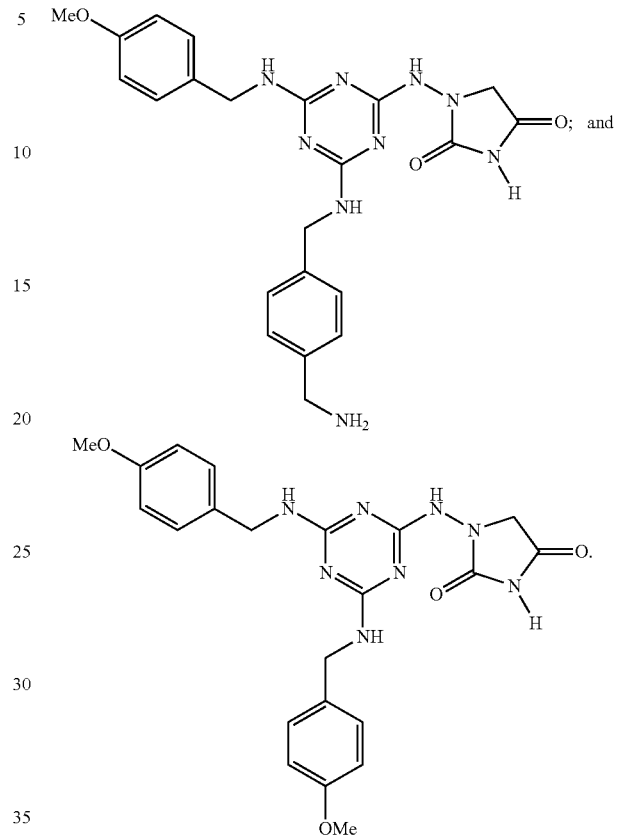

Chang et al (US 2004/0122009) have synthesized triazine compounds having antiproliferative effects similar to that of myoseverin. The Chang compounds are structurally distinct from the compounds of the present invention and are less active against cancer cell lines by orders of magnitude. In addition, the compounds disclosed in Chang et al have strikingly different biological activity to the compounds of the present invention. In their studies, Chang et al have found that their compounds show a close correlation between the $IC_{50}$ values required for tubulin polymerisation and for growth inhibition of U937 human leukemia cells (see Table 1, page 25). By contrast, the present inventors have found that, for compounds of the present invention, the concentration required for tubulin polymerisation was more than 1000 times greater than the $IC_{50}$ in cell proliferation assays.

As used herein, the term "halo" or "halogen" refers to fluorine (fluoro), chlorine (chloro), bromine (bromo) or iodine (iodo).

As used herein, the term "alkyl" either used alone or in compound terms such as NH(alkyl) or N(alkyl)$_2$, refers to monovalent straight chain or branched hydrocarbon groups. For example, suitable alkyl groups include, but are not limited to methyl, ethyl, n-propyl, isopropyl, n-butyl, sec-butyl, and tert-butyl.

As understood by a person skilled in the art, the term "$C_{1-4}$alkyl" means a straight or branched chain with 1, 2, 3 or 4 carbon atoms or a range comprising any of two of those integers.

The term "aryl" as used herein, refers to a $C_6$-$C_{10}$ aromatic hydrocarbon group, for example phenyl or naphthyl.

The term "cycloalkyl" as used herein, refers to cyclic hydrocarbon groups. Suitable cycloalkyl groups include, but are not limited to cyclopropyl, cyclobutyl, cyclopentyl and cyclohexyl.

As understood by a person skilled in the art, the term "$C_{3-6}$cycloalkyl" means a cycloalkyl group with 3, 4, 5, or 6 carbon atoms or a range comprising any of two of those integers.

The term "alkylaryl" includes, for example, benzyl.

Amine nitrogens may be protected by suitable nitrogen protecting groups (see "Protective Groups in Organic Synthesis" Theodora Greene and Peter Wuts, third edition, Wiley Interscience, 1999).

The salts of the compound of formula I are preferably pharmaceutically acceptable, but it will be appreciated that non-pharmaceutically acceptable salts also fall within the scope of the present invention, since these are useful as intermediates in the preparation of pharmaceutically acceptable salts.

The term "pharmaceutically acceptable derivative" may include any pharmaceutically acceptable salt, hydrate or prodrug, or any other compound which upon administration to a subject, is capable of providing (directly or indirectly) a compound of formula I or an active metabolite or residue thereof.

Suitable pharmaceutically acceptable salts include, but are not limited to, salts of pharmaceutically acceptable inorganic acids such as hydrochloric, sulphuric, phosphoric, nitric, carbonic, boric, sulfamic, and hydrobromic acids, or salts of pharmaceutically acceptable organic acids such as acetic, propionic, butyric, tartaric, maleic, hydroxymaleic, fumaric, malic, citric, lactic, mucic, gluconic, benzoic, succinic, oxalic, phenylacetic, methanesulphonic, toluenesulphonic, benzenesulphonic, salicylic, sulphanilic, aspartic, glutamic, edetic, stearic, palmitic, oleic, lauric, pantothenic, tannic, ascorbic and valeric acids.

Base salts include, but are not limited to, those formed with pharmaceutically acceptable cations, such as sodium, potassium, lithium, calcium, magnesium, zinc, ammonium; alkylammonium (such as salts formed from triethylamine) and alkoxyammonium (such as those formed with ethanolamine). Base salts also include salts formed from ethylenediamine, choline; and amino acids (such as arginine, lysine or histidine). General information on types of pharmaceutically acceptable salts and their formation is known to those skilled in the art and is as described in general texts such as "*Handbook of Pharmaceutical Salts*" P. H. Stahl, C. G. Wermuth, 1$^{st}$ edition, 2002, Wiley-VCH.

Basic nitrogen-containing groups may be quaternised with such agents as lower alkyl halide, such as methyl, ethyl, propyl, and butyl chlorides, bromides and iodides; dialkyl sulfates like dimethyl and diethyl sulfate; and others.

Hydroxyl groups may be esterified with groups including lower alkyl carboxylic acids, such as acetic acid and 2,2-dimethylpropionic acid, sulfonated with groups including alkyl sulfonic acids, such as methyl sulfonic acid or glycosylated to form glucuronide derivatives.

This invention also encompasses pharmaceutical compositions containing prodrugs of compounds of formula I. This invention also encompasses methods of treating or preventing cancer in a subject by administering prodrugs of compounds of the formula I. Compounds of formula I having free amino, amido, hydroxy or carboxylic groups can be converted into prodrugs.

Prodrugs include compounds wherein an amino acid residue, or a polypeptide chain of two or more (eg, two, three or four) amino acid residues which are covalently joined to free amino, hydroxy and carboxylic acid groups of compounds of formula I. The amino acid residues include the 20 naturally occurring amino acids commonly designated by three letter symbols and also include, 4-hydroxyproline, hydroxylysine, demosine, isodemosine, 3-methylhistidine, norvlin, beta-alanine, gamma-aminobutyric acid, citrulline, homocysteine, homoserine, ornithine and methionine sulfone. Prodrugs also include compounds wherein carbonates, carbamates, amides and alkyl esters which are covalently bonded to the above substituents of formula I through the carbonyl carbon prodrug sidechain. Prodrugs also include phosphate derivatives of compounds of formula I (such as acids, salts of acids, or esters) joined through a phosphorus-oxygen bond to a free hydroxyl of compounds of formula I.

It will also be recognised that the compounds of formula I may possess asymmetric centres and are therefore capable of existing in more than one stereoisomeric form. The invention thus also relates to compounds in substantially pure isomeric form at one or more asymmetric centres eg., greater than about 90% ee, such as about 95% or 97% ee or greater than 99% ee, as well as mixtures, including racemic mixtures, thereof.

Such isomers may be prepared by asymmetric synthesis, for example using chiral intermediates, or by chiral resolution.

In one embodiment the present invention provides a method of treatment of cancer in a subject comprising administering to said subject an effective amount of a compound of the present invention or a pharmaceutically acceptable derivative, salt or prodrug thereof.

In another embodiment the present invention provides the use of a compound of the present invention in the preparation of a medicament for the treatment of cancer.

In another embodiment the present invention provides a compound for use in the treatment of cancer.

Preferably, the cancer is colon cancer, non-small lung cancer, brain cancer or breast cancer.

The present inventors found that triazines of the present invention are at least as effective as Taxol in inducing G2/M block at their optimal concentration. However, whereas Taxol acts by stabilising tubulin polymerization, further experiments showed that triazine-induced tubulin polymerization was minimal and occurred at doses far exceeding their potency as mitotic blockers.

Therefore, in one embodiment the cancer is resistant to taxanes, for example paclitaxel, docetaxel and carbazitaxel.

In one embodiment the cancer is resistant to mitotic inhibitors, wherein the mitotic inhibitors directly interfere with the assembly and disassembly of tubulin.

In one embodiment the present invention provides a pharmaceutical composition comprising a compound of the present invention and a pharmaceutically acceptable carrier, diluent or excipient.

The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavours, etc.) according to techniques such as those well known in the art of pharmaceutical formulation.

The compounds of the present invention may be administered by any suitable means, for example, parenterally, such as by subcutaneous, intravenous, intramuscular, or intracisternal injection or infusion techniques (e.g., as sterile injectable aqueous or non-aqueous solutions or suspensions).

Pharmaceutical formulations include those for oral, rectal, nasal, topical (including buccal and sub-lingual), vaginal or parenteral (including intramuscular, sub-cutaneous and intravenous) administration or in a form suitable for administration by inhalation or insufflation. The compounds of the invention, together with a conventional adjuvant, carrier or diluent, may thus be placed into the form of pharmaceutical compositions and unit dosages thereof, and in such form may be employed as solids, such as tablets or filled capsules, or liquids as solutions, suspensions, emulsions, elixirs or capsules filled with the same, all for oral use, in the form of suppositories for rectal administration; or in the form of sterile injectable solutions for parenteral (including subcutaneous) use.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

The subjects treated in the above method are mammals, including, but not limited to, cows, sheep, goats, horses, dogs, cats, guinea pigs, rats or other bovine, ovine, equine, canine, feline, rodent or murine species, and preferably a human being, male or female.

The term "effective amount" means the amount of the subject composition that will elicit the biological or medical response of a tissue, system, animal or human that is being sought by the researcher, veterinarian, medical doctor or other clinician.

As would be understood by those skilled in the art of treating cancer, the term "treatment" does not necessarily mean that the cancer is completely cured. The term "treatment" encompasses any inhibition of replication of cancer cells and/or reduction in the tumor size in the subject being treated.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention to the individual in need of treatment.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The pharmaceutical composition and method of the present invention may further comprise other therapeutically active compounds which are usually applied in the treatment of the above mentioned pathological conditions. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

When other therapeutic agents are employed in combination with the compounds of the present invention they may be used for example in amounts as noted in the Physician Desk Reference (PDR) or as otherwise determined by one of ordinary skill in the art.

In the treatment or prevention of conditions which require inhibition of replication of cancer cells and/or reduction in the tumor size, an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Any discussion of documents, acts, materials, devices, articles or the like which has been included in the present specification is not to be taken as an admission that any or all of these matters form part of the prior art base or were common general knowledge in the field relevant to the present invention as it existed before the priority date of each claim of this application.

In order that the nature of the present invention may be more clearly understood preferred forms thereof will now be described by reference to the following non-limiting Examples.

EXAMPLES

Example 1

Synthetic Chemistry

A rapid, high-yield, synthesis protocol was developed which allowed modification of the 1,3,5-triazine scaffold to yield a range of trazine substituted derivatives

Example 1.1

Synthetic Method for the Preparation of 1-[4,6-Bis-(4-methoxybenzylamino)-{1,3,5}-triazin-2-yl-amino]-imidazolidine-2,4-dione (compound 1)

Part A Preparation of 1-(4,6-dichloro-[1,3,5]-triazin-2-yl-amino)-imidazolidine-2,4-dione

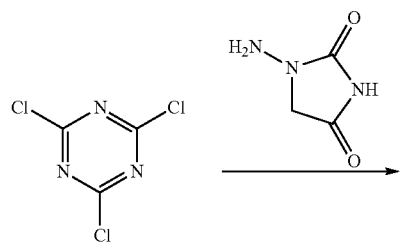

An ice-cold suspension of 1-aminohydantoin hydrochloride (457 mg, 3.0 mmol), cyanuric chloride (500 mg, 2.73 mmol) and sodium bicarbonate (505 mg, 6 mmol) in acetonitrile (5 mL) was stirred under an atmosphere of nitrogen for 2 h and then stirred at room temperature for 20 h. The reaction mixture was evaporated to dryness under reduced pressure and the residue was extracted with ethyl acetate and the ethyl acetate was separated and dried ($MgSO_4$). The crude product (770 mg) gave a single spot on thin layer chromatography [silica; $CH_2Cl_2$/MeOH (10:1)] and was used in the next step without further purification. $^1$H NMR ($CD_3CN$): δ=4.11 (s, 2H); 8.71 (s, 1H); 8.85 (s, 1H).

Part B Preparation of 1-[4,6-Bis-(4-methoxybenzylamino)-{1,3,5}-triazin-2-yl-amino]-imidazolidine-2,4-dione (compound 1)

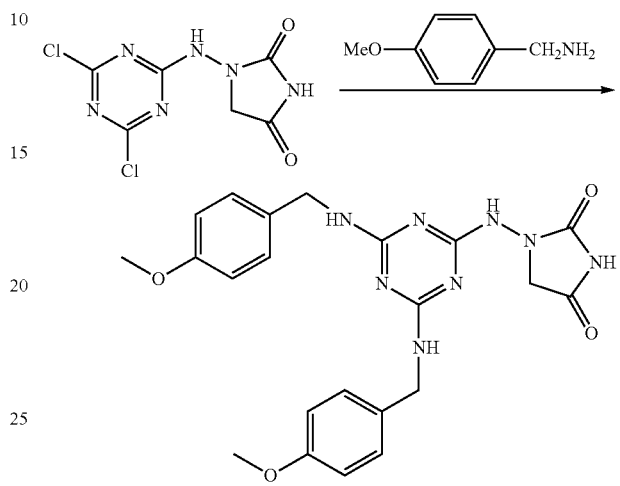

To a stirred suspension of 1-(4,6-dichloro-[1,3,5]-triazin-2-yl-amino)-imidazolidine-2,4-dione (770 mg, 2.93 mmol) and potassium carbonate (2.42 g, 17.6 mmol) in acetonitrile (20 mL) at room temperature was added 4-methoxybenzylamine (0.96 mL, 7.32 mmol). The reaction mixture was stirred for 24 h at room temperature under an atmosphere of nitrogen and then the solvent was removed under reduced pressure. The residue was extracted with ethyl acetate and the ethyl acetate was dried ($MgSO_4$) and evaporated to give the crude product which was purified by flash chromatography on silica using $CH_2Cl_2$/MeOH (50:1→10:1) as eluent. The pure product was isolated as a colourless solid (587 mg, 43%). $^1$H NMR ($d_6$ DMSO): δ=3.67 (s, 6H); 3.96 and 4.05 (2 s, total 214); 4.20 and 4.32 (2 s, total 4H); 6.80 (bs, 4H); 7.13-7.39 (m, 6H); 8.67, 8.85 and 8.99 (2 s, total 1H); 11.0 (bs, 1H). Mass spectrum (ES+) 465 (M+H).

Example 1.2

Synthetic Method for the Preparation of 1-[4-(4-aminomethyl-benzylamino)-6-(4-methoxybenzylamino)-{1,3,5}-triazin-2-yl-amino]-imidazolidine-2, 4-dione, HCl salt (compound 2)

Part A Preparation of 1-[4-chloro-6-(4-N-Boc-aminomethyl)-benzylamino-{1,3,5}-triazin-2-yl-amino]-imidazolidine-2,4-dione

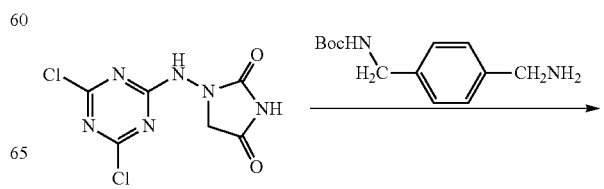

-continued

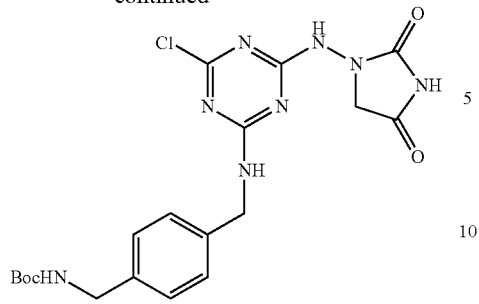

To a stirred suspension of 1-(4,6-dichloro-[1,3,5]-triazin-2-yl-amino)-imidazolidine-2,4-dione (Example 1.1, Part A)(590 mg, 2.24 mmol) and potassium carbonate (681 mg, 4.94 mmol) in dry dimethylformamide (DMF, 10 mL) was added 4-(N-Boc-aminomethyl)-benzylamine (582 mg, 2.47 mmol). The mixture was stirred at room temperature for 20 h and then poured into a mixture of water and ethyl acetate. The resultant emulsion was filtered and then the organic layer was separated, dried and evaporated to give the crude product (576 mg, 55%) as a yellow solid. Mass spectrum (ESI+): 946 (2M+Na), 924 (2M+H).

Part B Preparation of 1-[4-(4-aminomethyl-benzylamino)-6-(4-methoxybenzylamino)-{1,3,5}-triazin-2-yl-amino]-imidazolidine-2,4-dione, HCl salt (compound 2)

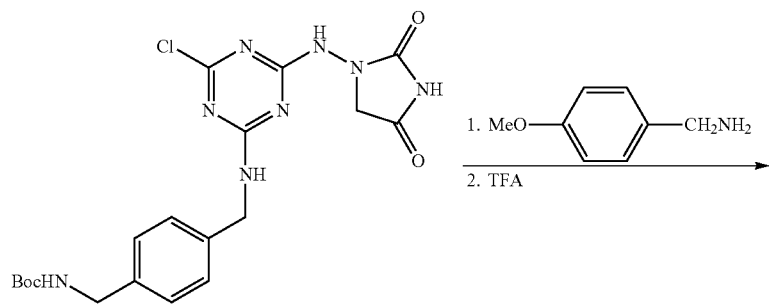

To a stirred suspension of 1-[4-chloro-6-(4-N-Boc-aminomethyl)-benzylamino-{1,3,5}-triazin-2-yl-amino]-imidazolidine-2,4-dione (Example 1.2, Part A) (200 mg, 0.43 mmol) and potassium carbonate (131 mg, 0.95 mmol) in DMF (5 mL) was added 4-methoxybenzylamine (0.06 mL, 0.48 mmol). The reaction mixture was stirred at 35° for 18 h and then poured into water and extracted with ethyl acetate. The resultant emulsion was filtered and the ethyl acetate layer was separated and evaporated to give the N-Boc product as an oily residue (90 mg, 37%). Mass spectrum (ESI+): 1127 (2M+H), 564 (M+H). The N-Boc material (90 mg) was dissolved in dichloromethane/trifluoroacetic acid (1:1, 3 mL) and stirred at room temperature under nitrogen for 2 h. The solvent and excess TFA was removed under reduced pressure and the residue was dissolved in methanol (5 mL) and treated with a solution of hydrogen chloride in diethyl ether (0.08 mL of a 2M solution). The methanol was removed under reduced pressure and the residue was recrystallised from methanol/acetonitrile to give the crude hydrochloride salt as an off-white solid (49 mg, 62%). $^1$H NMR ($d_6$ DMSO): δ=3.72 (s, 3H); 3.96-4.12 (m, 6H); 4.32-4.52 (m, 4H); 6.84 (brs, 2H); 7.16-7.51 (m, 6H); 8.4 and 8.5 (brd, 6H); 11.3 (s, 1H). Mass spectrum (ES+): 464 (M+H).

Example 1.3

Synthetic Methods for the Preparation of triazine-imidazolidine-diones

Preparation of 5-[4,6-Bis-(4-methoxy-benzylamino)-[1,3,5]-triazin-2-ylamino]-3-methyl-imidazolidine-2,4-dione (compound 3)

Part A Preparation of 1-Methyl-imidazolidine-2,4,5-trione

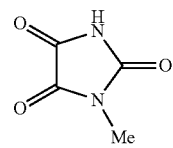

To an ice-cold solution of 1-methylurea (200 mg, 2.70 mmol) in dry tetrahydrofuran (6 mL) was added oxalyl chloride (0.26 mL, 2.97 mmol) dropwise, under a nitrogen atmosphere. The reaction mixture was stirred at 0-5° for 2 h and then allowed to warm to room temperature for 1 h before being diluted with water. The product was extracted with ethyl acetate, and the extracts were washed with water, dried and evaporated to give the product as an off-white solid (326 mg, 94%), mp 146-149° C. (lit. 145-148° C.).

Part B Preparation of 5-Benzylamino-3-methyl-imidazole-2,4-dione

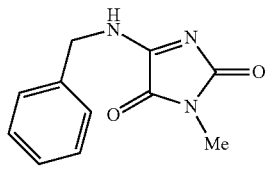 [SMILES: CN1C(=O)N=C(NCc2ccccc2)C1=O]

To a solution of 1-methyl-imidazolidine-2,4,5-trione (Example 1.3, Part A) (800 mg, 6.25 mmol), imidazole (467 mg, 6.87 mmol), N,N-dimethylaminopyridine (cat.) and triethylamine (1.82 mL, 13.1 mmol) in chloroform (13 mL) was added chlorotrimethylsilane (1.67 mL, 13.1 mmol) dropwise at room temperature under a nitrogen atmosphere, and the reaction mixture was stirred for 2 h. Benzylamine (0.75 mL, 6.87 mmol) was added and the reaction mixture was stirred for a further 22.5 h. The reaction mixture was diluted with chloroform and water and the chloroform extracts were dried and evaporated. The crude product was purified by column chromatography (PS with gradient elution to DCM:EtOAc 3:1) to give the product as a colourless solid (838 mg, 62%), mp 152-154° C. $\delta_H$ (300 MHz, CD$_3$CN) 7.95 (v br s, 1H, NH), 7.41-7.27 (m, 5H, PhH), 4.64 (s, 2H, CH$_2$), 2.95 (s, 3M, CH$_3$). Mass spectrum (ESI) m/z 218 (M+H).

Part C Preparation of 5-Amino-3-methyl-imidazolidine-2,4-dione

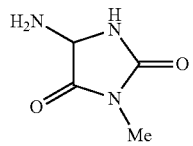

To a solution of 5-benzylamino-3-methyl-imidazole-2,4-dione (Example 1.3, Part B) (400 mg, 1.84 mmol) in ethanol/ethyl acetate (50 mL, 1:1) was added 10% Pd/C catalyst (195 mg, 0.18 mmol). The flask was evacuated and filled with hydrogen three times and then stirred at room temperature for 23 h. After this period, the reaction mixture was filtered through celite and the filtrate was evaporated to give the product as a colourless solid (214 mg, 90%), mp 122-125° C. $\delta_H$ (300 MHz, CD$_3$CN) 6.31 (br s, 1H, NH), 4.68 (d, J 1.5 Hz, 1H, CH), 2.87 (s, 3H, CH$_3$). $\delta_H$ (300 MHz, D$_2$O) 4.95 (s, 1H, CH), 2.96 (s, 3H, CH$_3$). $\delta_C$ (75 MHz, D$_2$O) 175.6, 158.5, 64.0 (CH), 24.3 (CH$_3$).

Part D Preparation of 5-(4,6-Dichloro-[1,3,5]triazin-2-ylamino)-3-methyl-imidazolidine-2,4-dione

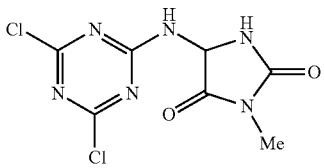 [SMILES: CN1C(=O)NC(Nc2nc(Cl)nc(Cl)n2)C1=O]

An ice-cold suspension of 5-amino-3-methyl-imidazolidine-2,4-dione (Example 1.3, Part C) (266 mg, 2.06 mmol), cyanuric chloride (415 mg, 2.27 mmol) and sodium bicarbonate (191 mg, 2.27 mmol) in acetonitrile (15 mL) was stirred over an ice bath under a nitrogen atmosphere for 1 h, and then allowed to stir at room temperature for 22 h. The solvent was evaporated, and the crude product was extracted with ethyl acetate. The organic layer was dried and evaporated, and the crude product was purified by column chromatography (PS with gradient elution to DCM:EtOAc 1:1) to afford the product as a cream solid (448 mg, 78%). $\delta_H$ (300 MHz, CD$_3$CN) 7.50 (br s, 1H, NH), 6.56 (br s, 1H, NH), 5.60 (dd, J 7.8, 1.8 Hz, 1H, CH), 2.97 (s, 3H, CH$_3$). Mass spectrum (ESI) m/z 259 [M+H (OH for Cl exchanged ion)].

Part E Preparation of 5-[4,6-Bis-(4-methoxy-benzylamino)-[1,3,5]-triazin-2-ylamino]-3-methyl-imidazolidine-2,4-dione (compound 3)

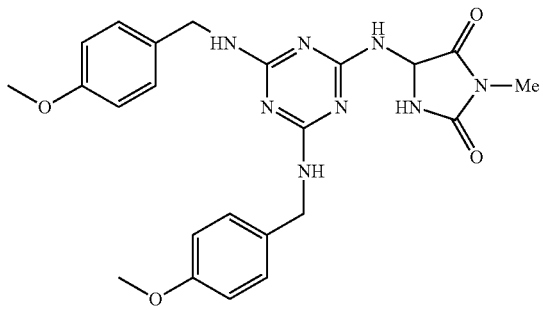 [SMILES: COc1ccc(CNc2nc(NCc3ccc(OC)cc3)nc(NC3NC(=O)N(C)C3=O)n2)cc1]

To a stirred suspension of 5-(4,6-dichloro-[1,3,5]triazin-2-ylamino)-3-methyl-imidazolidine-2,4-dione (Example 1.3, Part D) (193 mg, 0.70 mmol) and potassium carbonate (212 mg, 1.53 mmol) in acetonitrile (15 mL) at 5° was added 4-methoxybenzylamine (0.10 mL, 0.77 mmol) dropwise. The suspension was stirred at ice temperature for 1 h and then at room temperature for 24 h. Water was added to the reaction mixture which was then extracted with ethyl acetate. The crude product was applied to a silica column and eluted, starting with a mixture of dichloromethane:ethyl acetate (10:1), then 5:1 and eventually dichloromethane:methanol (20:1). The early fractions yielded the intermediate mono-substituted 5-[4-chloro-6-(4-methoxy-benzylamino)-[1,3,5]-triazin-2-ylamino]-3-methyl-imidazolidine-2,4-dione (133 mg, 51%) and later fractions gave the di-benzylamino product (112 mg, 34%) (Found: C, 55.46; H, 4.66; N, 18.39%. C$_{21}$H$_{20}$N$_6$O$_6$ requires C, 55.75; H, 4.46; N, 18.58). $\delta_H$ (300 MHz, CD$_3$CN): 7.19 (br d, 4H, Ar), 6.84 (br d, 4H, Ar), 6.35 (br s, 1H, NH), 5.9-5.8 (br, 3H, NH), 5.46 (br d, 1H, CH), 4.36 (s, 4H, CH$_2$), 3.74 (s, 6H, OMe), 2.9-2.8 (br, 3H, NMe). Mass spectrum (EST) m/z 479 [M+H].

Example 1.4

Preparation of 5-[4-(4-aminomethyl-benzylamino)-6-(4-methoxybenzylamino)-[1,3,5]-triazin-2-ylamino]-3-methyl-imidazolidine-2,4-dione (compound 4)

Part A 5-[4-chloro-6-(N-Boc-{4-aminomethyl}-benzylamino)-[1,3,5]-triazin-2-yl amino]-3-methyl-imidazolidine-2,4-dione

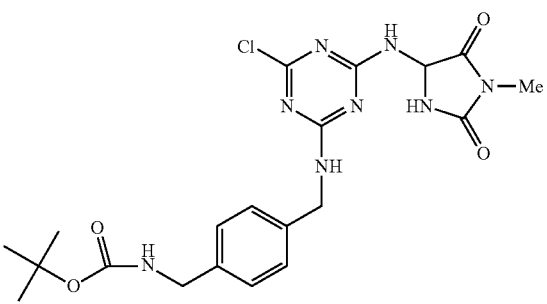 [SMILES: CN1C(=O)NC(Nc2nc(Cl)nc(NCc3ccc(CNC(=O)OC(C)(C)C)cc3)n2)C1=O]

To a stirred suspension of 5-(4,6-dichloro-[1,3,5]triazin-2-ylamino)-3-methyl-imidazolidine-2,4-dione (Example 1.3, Part D) (300 mg, 1.08 mmol) and potassium carbonate (329 mg, 2.38 mmol) in dimethylformamide (5 mL) at room temperature was added N-Boc-(4-aminomethyl)-benzylamine (281 mg, 1.19 mmol). The reaction mixture was stirred at room temperature for 4 h and then diluted with water and ethyl acetate. The ethyl acetate layer was separated, dried and evaporated to give the crude product which was used directly in the next step.

Part B Preparation of 5-[4-{(N-Boc-4-aminomethyl)-benzylamino}-6-(4-methoxy benzylamino)-[1,3,5]-triazin-2-ylamino]-3-methyl-imidazolidine-2,4-dione (compound 4(B))

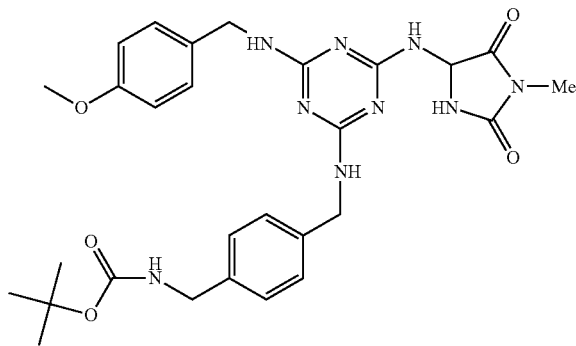 [SMILES: COc1ccc(CNc2nc(NCc3ccc(CNC(=O)OC(C)(C)C)cc3)nc(NC3NC(=O)N(C)C3=O)n2)cc1]

To a stirred suspension of 5-[4-chloro-6-(N-Boc-{4-aminomethyl}-benzylamino)-[1,3,5]-triazin-2-yl amino]-3-methyl-imidazolidine-2,4-dione (Example 1.4, Part A) (377 mg, 0.79 mmol) and potassium carbonate (240 mg, 1.74 mmol) in dimethylformamide (5 mL) at 30° was added 4-methoxybenzylamine (0.12 mL, 0.95 mmol). The reaction mixture was stirred at 30° for 18 h and then diluted with water and extracted with ethyl acetate. The ethyl acetate layer was washed with dilute hydrochloric acid and then separated, dried and concentrated to give the crude product which was purified by chromatography on silica gel using dichloromethane as initial eluent and gradually increasing the polarity to dichloromethane:methanol (20:1). The product was obtained as a white solid (71 mg, 16%). NMR spectrum $\delta_H$ (300 MHz, CD$_3$CN): 7.16 (br s, 6H, Ar), 6.82 (br d, 2H, Ar), 6.5 (br s, 1H, NH), 6.1-5.7 (br m, 4H, NH), 5.47 (br d, 1H, CH), 4.5-4.3 (br, 4H, CH$_2$), 4.15 (d, 2H, CH$_2$) 3.73 (s, 3H, OMe), 2.9-2.7 (br, 3H, NMe), 1.39 (s, 9H, Boc).

Part C Preparation of 5-[4-(4-aminomethyl-benzylamino)-6-(4-methoxybenzylamino)-[1,3,5]-triazin-2-ylamino]-3-methyl-imidazolidine-2,4-dione (compound 4)

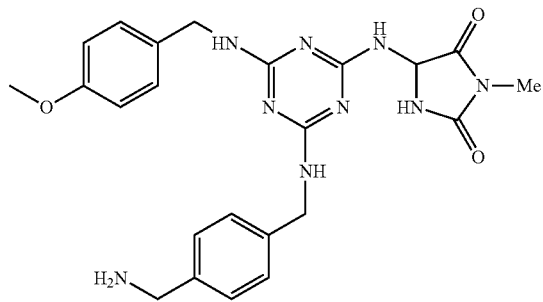 [SMILES: COc1ccc(CNc2nc(NCc3ccc(CN)cc3)nc(NC3NC(=O)N(C)C3=O)n2)cc1]

Trifluoroacetic acid (2 mL) was added to a stirred solution of 5-[4-{(N-Boc-4-aminomethyl)-benzylamino}-6-(4-methoxybenzylamino)-[1,3,5]-triazin-2-ylamino]-3-methyl-imidazolidine-2,4-dione (Example 1.4, Part B) (63 mg, 0.11 mol) in dichloromethane (2 mL) at room temperature. After 3 h the TFA and solvent were removed by evaporation under reduced pressure and extra dichloromethane was added and again removed to help drive off any remaining excess TFA. The crude product was dissolved in dry methanol and a solution of hydrogen chloride in ether (2M, 0.05 mL) was added. The reaction mixture was stirred at room temperature for 15 minutes and then concentrated and the residue was crystallized by triturating with methanol/acetonitrile under ice cooling. The resultant pale pink solid was collected by filtration to give the product as the HCl salt (48 mg, 86%). NMR spectrum $\delta_H$ (300 MHz, d$_6$-DMSO): 8.9-8.2 (br m, 6H, NH), 7.4-7.1 (br m, 6H, Ar), 6.85 (d, 2H, Ar), 5.6 (br, 1H, CH), 4.5-4.2 (br, 4H, CH$_2$), 3.95 (br s, 2H, CH$_2$) 3.70 (s, 3H, OMe), 2.8-2.6 (br, 3H, NMe); Mass spectrum (ESI) m/z 478 [M+H].

Example 1.5

Preparation of 5-[4-(4-methyl-benzylamino)-6-(4-methoxybenzylamino)-[1,3,5]-triazin-2-ylamino]-3-methyl-imidazolidine-2,4-dione (compound 5)

Part A Preparation of 5-[4-chloro-6-(4-methyl-benzylamino)-[1,3,5]-triazin-2-ylamino]-3-methyl-imidazolidine-2,4-dione

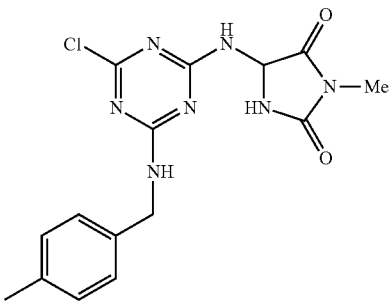 [SMILES: Cc1ccc(CNc2nc(Cl)nc(NC3NC(=O)N(C)C3=O)n2)cc1]

To a stirred suspension of 5-(4,6-dichloro-[1,3,5]triazin-2-ylamino)-3-methyl-imidazolidine-2,4-dione (Example 1.3, Part D) (200 mg, 0.72 mmol) and potassium carbonate (219 mg, 1.59 mmol) in dimethylformamide (5 mL) at room temperature was added 4-methyl-benzylamine (0.1 mL, 0.79 mmol). The reaction mixture was stirred at 35° for 24 h and then diluted with water and ethyl acetate. The ethyl acetate layer was separated, dried and evaporated to give the crude product which was used directly in the next step.

Part B Preparation of 5-[4-(4-methyl-benzylamino)-6-(4-methoxybenzylamino)-[1,3,5]-triazin-2-ylamino]-3-methyl-imidazolidine-2,4-dione (compound 5)

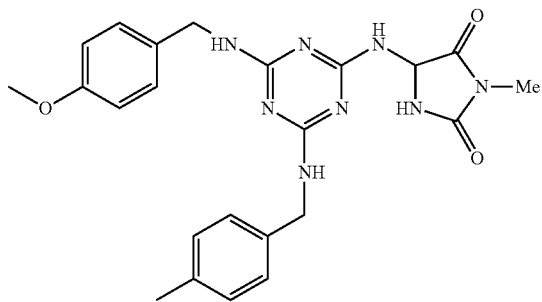 [SMILES: COc1ccc(CNc2nc(NCc3ccc(C)cc3)nc(NC3NC(=O)N(C)C3=O)n2)cc1]

To a stirred suspension of 5-[4-chloro-6-(4-methyl-benzylamino)-[1,3,5]-triazin-2-ylamino]-3-methyl-imidazolidine-2,4-dione (Example 1.5, Part A) (80 mg, 0.22 mmol) and potassium carbonate (67 mg, 0.49 mmol) in dimethylformamide (5 mL) at 35° was added 4-methoxybenzylamine (0.03 mL, 0.24 mmol). The reaction mixture was stirred at 35° for 20 h and then diluted with water and extracted with ethyl acetate. The ethyl acetate layer was dried and concentrated to give the crude product as a foam (79 mg, 77%). NMR spectrum $\delta_H$ (300 MHz, CD$_3$CN): 7.2-7.0 (br m, 7H, Ar+NH), 6.8 (br d, 2H, Ar), 6.5 (br, 1H, NH), 6.1-5.8 (br m, 2H, NH), 5.45 (br d, 1H, CH), 4.5-4.3 (br, 4H, CH$_2$), 4.15 (d, 2H, CH$_2$) 3.74 (s, 3H, OMe), 2.9-2.7 (br, 3H, NMe), 2.3 (s, 3H, Me). Mass spectrum (ESI) m/z 463 [M+H].

Example 1.6

Preparation of 5-[4,6-Bis-(4-methoxy-benzylamino)-[1,3,5]-triazin-2-ylamino]-3-n-butyl-imidazolidine-2,4-dione (compound 6)

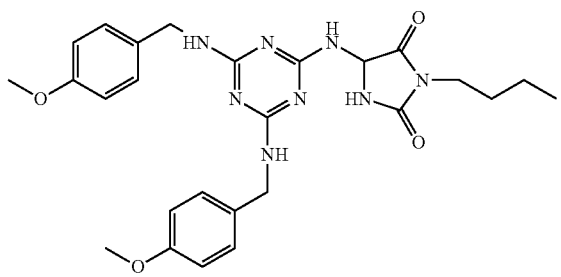 [SMILES: CCCCN1C(=O)NC(Nc2nc(NCc3ccc(OC)cc3)nc(NCc3ccc(OC)cc3)n2)C1=O]

The title compound was prepared using essentially the same reaction sequence and conditions as described in Example 1.3, Parts B to E, but using 1-(n-butyl)-imidazolidine-2,4,5-trione in place of the 1-methyl-imidazolidine-2,4,5-trione. The product from the final step was purified by chromatography and characterized by NMR and Mass spectroscopy. NMR spectrum $\delta_H$ (300 MHz, CD$_3$CN): 7.19 (br d, 4H, Ar), 6.84 (br d, 4H, Ar), 6.38 (br s, 1H, NH), 6.0-5.7 (br, 3H, NH), 5.5 (br d, 1H, CH), 4.36 (s, 4H, CH$_2$), 3.74 (s, 6H, OMe), 3.38 (t, 2H, NCH$_2$); 1.52 (m, 2H, CH$_2$); 1.28 (m, 2H, CH$_2$); 0.89 (d, 3H, Me). Mass spectrum (ESI) m/z 521 [M+H].

Example 1.7

Preparation of 5-[4,6-Bis-(4-methoxy-benzylamino)-[1,3,5]-triazin-2-ylamino]-3-n-propyl-imidazolidine-2,4-dione (compound 7)

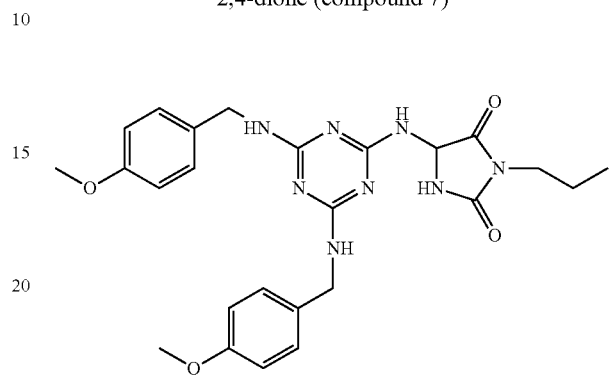

The title compound was prepared using essentially the same reaction sequence and conditions as described in Example 1.3, Parts B to E, but using 1-(n-propyl)-imidazolidine-2,4,5-trione in place of the 1-methyl-imidazolidine-2,4,5-trione. The product from the final step was purified by chromatography and characterized by NMR and Mass spectroscopy. NMR spectrum $\delta_H$ (300 MHz, d$_6$DMSO): 8.31 (s, 1H, NH); 7.5 (br, 1H, NH); 7.1-7.3 (br, 6H, Ar+NH), 6.83 (br d, 4H, Ar), 5.5 (br d, 1H, CH), 4.32 (s, 4H, CH$_2$), 3.78 (s, 6H, OMe), 3.34 (br, 2H, NCH$_2$); 1.46 (m, 2H, CH$_2$); 0.79 (br, 3H, Me). Mass spectrum (ESI) m/z 507 [M+H].

Example 1.8

Preparation of 5-[4,6-Bis-(4-methoxy-benzylamino)-[1,3,5]-triazin-2-ylamino]-3-phenyl-imidazolidine-2,4-dione (compound 8)

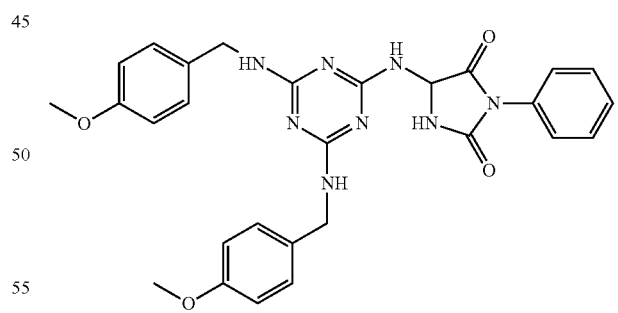

The title compound was prepared using essentially the same reaction sequence and conditions as described in Example 1.3, Parts B to E, but using 1-phenyl-imidazolidine-2,4,5-trione in place of the 1-methyl-imidazolidine-2,4,5-trione. The product from the final step was purified by chromatography and characterized by NMR and Mass spectroscopy. NMR spectrum $\delta_H$ (300 MHz, CD$_3$CN): 8.07 (s, 1H, NH); 7.4-7.0 (br, 9H, Ar+NH); 6.9-6.6 (br, 5H, Ar+NH), 6.2-5.5 (br, 3H, NH+CH), 5.5 (br d, 1H, CH), 4.38 (s, 4H, CH$_2$), 3.73 (s, 6H, OMe). Mass spectrum (ESI) m/z 541 [M+H].

Example 1.9

Preparation of 5-[4,6-Bis-(4-methoxy-phenoxy)-[1,3,5]-triazin-2-ylamino]-3-methyl-imidazolidine-2,4-dione (compound 9)

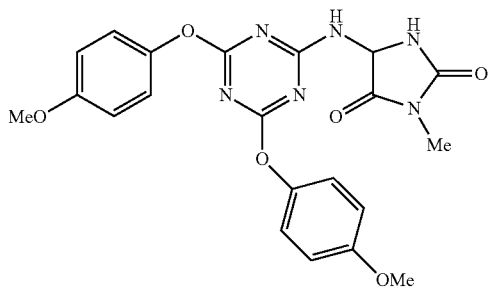 [SMILES: COc1ccc(Oc2nc(NC3NC(=O)N(C)C3=O)nc(Oc3ccc(OC)cc3)n2)cc1]

A suspension of 5-amino-3-methyl-imidazolidine-2,4-dione (Example 1.3, Part C) (80 mg, 0.29 mmol), p-methoxyphenol (39 mg, 0.32 mmol) and potassium carbonate (88 mg, 0.64 mmol) in acetonitrile (5 mL) was stirred at room temperature under a nitrogen atmosphere for 18 h. The reaction mixture was diluted with ethyl acetate and water, and the crude product was extracted with ethyl acetate. The organic layer was dried and evaporated, and the crude product was purified by column chromatography (silica; dichloromethane:ethyl acetate, with the solvent ratio increasing from 10:1 to 1:2) and then recrystallized from acetonitrile to give the title compound as a colourless solid (17 mg, 13%). (Found: C, 55.5; H, 4.7; N, 18.4%. $C_{21}H_{20}N_6O_6$ requires C, 55.8; H, 4.5; N, 18.6%). $\delta_H$ (300 MHz, $(CD_3)_2CO$) 7.81 (d, J 8.1 Hz, 1H, NH), 7.40 (s, 1H, NH), 7.08 (d, J 9.0 Hz, 2H, ArH (ortho to OPh attach)), 7.07 (d, J 9.0 Hz, 2H, ArH (ortho to OPh attach)), 6.92 (d, J 9.0 Hz, 4H, ArH (ortho to $OCH_3$ attach)), 5.73 (d, J 8.4 Hz, 1H, CH), 3.81 (s, 6H, $OCH_3$), 2.77 (s, 31-1, $NCH_3$). Mass spectrum (ESI) m/z 453 (72%, $MH^+$).

Example 1.10

Preparation of 5-[4,6-Bis-(4-methoxy-phenylamino)-[1,3,5]triazin-2-ylamino]-3-methyl-imidazolidine-2,4-dione (compound 10)

Part A Preparation of 5-[4-Chloro-6-(4-methoxy-phenylamino)-[1,3,5]triazin-2-ylamino]-3-methyl-imidazolidine-2,4-dione

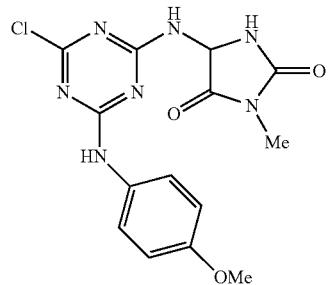 [SMILES: COc1ccc(Nc2nc(Cl)nc(NC3NC(=O)N(C)C3=O)n2)cc1]

A suspension of 5-amino-3-methyl-imidazolidine-2,4-dione (Example 1.3, Part C) (228 mg, 0.82 mmol), p-methoxyaniline (111 mg, 0.90 mmol) and sodium bicarbonate (76 mg, 0.90 mmol) in acetonitrile (7 mL) was stirred at room temperature under a nitrogen atmosphere for 25 h. The solvent was evaporated, and the crude product was extracted with ethyl acetate. The organic layer was dried and evaporated and the crude product was purified by column chromatography (silica; dichloromethane:ethyl acetate starting with a solvent ratio of 10:1 and increasing the polarity to dichloromethane:methanol, 10:1) to afford the title compound as a cream solid (288 mg, 96%). $\delta_H$ (300 MHz, $(CD_3)_2CO$) 8.88 (br s, 0.5H, NH), 8.84 (br s, 0.5H, NH), 7.87 and 7.70 (2 br s, 1H, NH), 7.61 (br s, 1H, NH), 7.51 (d, J 9.0 Hz, 2H, ArH (ortho to NH attach)), 6.91 and 6.89 (2 d, J 8.7, 6.6 Hz, 2H ArH (ortho to O attach)), 5.82 (br d, J 7.8 Hz, 1H, CH), 3.79 (s, 3H, $OCH_3$), 2.95 (s, 1.4H, $NCH_3$), 2.73 (s, 1.6H, $NCH_3$). Mass spectrum (ESI) m/z 364 (100%, $MH^+$).

Part B Preparation of 5-[4,6-Bis-(4-methoxy-phenylamino)-[1,3,5]triazin-2-ylamino]-3-methyl-imidazolidine-2,4-dione (compound 10)

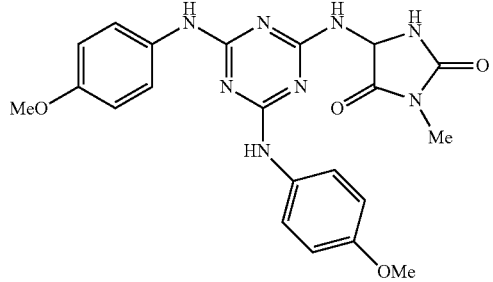 [SMILES: COc1ccc(Nc2nc(Nc3ccc(OC)cc3)nc(NC3NC(=O)N(C)C3=O)n2)cc1]

A suspension of 5-[4-chloro-6-(4-methoxy-phenylamino)-[1,3,5]triazin-2-ylamino]-3-methyl-imidazolidine-2,4-dione (Example 1.10, Part A) (50 mg, 0.14 mmol), p-methoxyaniline (25 mg, 0.21 mmol) and potassium carbonate (48 mg, 0.34 mmol) in anhydrous DMF (5 mL) was stirred under a nitrogen atmosphere for 18.5 h. The reaction mixture was diluted with water and the crude product was extracted with ethyl acetate. The organic layer was dried and evaporated, and the crude product was purified by column chromatography (silica; dichloromethane:ethyl acetate starting with a solvent ratio of 10:1 and increasing the polarity to dichloromethane:methanol, 10:1) to afford the product as a pale yellow solid (36 mg, 58%). $\delta_H$ (300 MHz, $(CD_3)_2CO$) 8.14 (br s, 2H, NH), 7.60 (br s, 4H, ArH (ortho to NH attach)), 7.43 (br s, 1H, NH), 6.91 (d, J 8.7 Hz, 1H, NH), 6.85 (d, J 9.0 Hz, 4H, ArH (ortho to O attach)), 5.91 (d, J 7.8 Hz, 1H, CH), 3.77 (s, 6H, $OCH_3$), 2.86 (br s, 2.0H, $NCH_3$), 2.73 (br s, 1.0H, $NCH_3$). Mass spectrum (ESI) m/z 451 (37%, $MH^+$).

Example 1.11

Preparation of 5-[4-(4-Hydroxy-phenylamino)-6-(4-methoxy-phenylamino)-[1,3,5]triazin-2-ylamino]-3-methyl-imidazolidine-2,4-dione (compound 11)

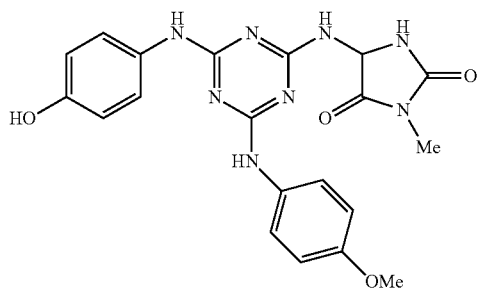 [SMILES: COc1ccc(Nc2nc(Nc3ccc(O)cc3)nc(NC3NC(=O)N(C)C3=O)n2)cc1]

A suspension of 5-[4-Chloro-6-(4-methoxy-phenylamino)-[1,3,5]triazin-2-ylamino]-3-methyl-imidazolidine-2,4-dione (Example 1.10, Part A) (76 mg, 0.05 mmol), p-aminophenol (50 mg, 0.46 mol) and potassium acetate (25 mg, 0.25 mmol) in anhydrous DMF (3 mL) was stirred under a nitrogen atmosphere over a 35° C. oil bath for 22 h. The reaction mixture was diluted with water, and the crude product was extracted with ethyl acetate. The organic layer was dried and evaporated and the crude product was purified by column chromatography (silica; dichloromethane:ethyl acetate starting with a solvent ratio of 10:1 and increasing the polarity to dichloromethane:methanol, 10:1) to afford the product as a fawn solid (24 mg, 33%). (Found: C, 54.1; H, 4.9; N, 24.3%. $C_{20}H_{20}N_8O_4$.MeOH requires C, 53.8; H, 5.2; N, 23.9%). $\delta_H$ (300 MHz, $CD_3CN$) 7.49 (br d, J 8.7 Hz, 2H, ArH (ortho to NH attach)), 7.37 (br s, 4H, NH and ArH (ortho to NH attach)), 6.87 (d, J 9.0 Hz, 2H, ArH (ortho to O attach)), 6.75 (d, J 9.0 Hz, 2H, ArH (ortho to O attach)), 6.70 (br s, 1H, OH), 6.48 (s, 1H, NH), 6.10 (br d, J 7.8 Hz, 1H, NH), 5.67 (d, J 7.8 Hz, 1H, CH), 3.78 (s, 3H, $OCH_3$), 2.88 (br s, 3H, $NCH_3$). Mass spectrum (ESI) m/z 437 (36%, MH+).

Example 1.12

Preparation of 5-[4-(4-Benzyloxy-phenylamino)-6-(4-methoxy-phenylamino)-[1,3,5]triazin-2-ylamino]-3-methyl-imidazolidine-2,4-dione (compound 12)

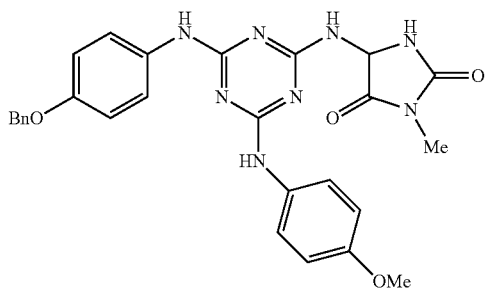

A suspension of 5-[4-Chloro-6-(4-methoxy-phenylamino)-[1,3,5]triazin-2-ylamino]-3-methyl-imidazolidine-2,4-dione (Example 1.10, Part A) (93 mg, 0.26 mmol), p-benzyloxyaniline hydrochloride (132 mg, 0.56 mmol) and cesium carbonate (184 mg, 0.56 mmol) in anhydrous DMF (5 mL) was stirred under a nitrogen atmosphere over a 30° C. oil bath for 19 h. The reaction mixture was diluted with water and the crude product was extracted with ethyl acetate. The organic layer was dried and evaporated and the crude product was purified by column chromatography (silica; dichloromethane:ethyl acetate starting with a solvent ratio of 10:1 and increasing the polarity to dichloromethane:methanol, 20:1). Recrystallization from PS/DCM/EtOAc gave the product as a cream solid (90 mg, 62%). (Found: C, 61.5; H, 5.1; N, 21.2%. $C_{27}H_{26}N_8O_4$ requires C, 61.6; H, 5.0; N, 21.3%). $\delta_H$ (300 MHz, $CD_3CN$) 7.58-7.30 (m, 11H, ArH (ortho to NH attach), PhH and 2 NH), 6.94 (d, J 8.7 Hz, 2H, ArH (ortho to O attach)), 6.87 (d, J 8.7 Hz, 2H, ArH (ortho to O attach)), 6.49 (br s, 1H, NH), 6.14 (m, 1H, NH), 5.67 (d, J 7.2 Hz, 1H, CH), 5.09 (s, 2H, $CH_2$), 3.78 (s, 3H, $OCH_3$), 2.88 (br s, 3H, $NCH_3$). Mass spectrum (ESI) m/z 527 (100%, MH+).

Example 1.13

Preparation of 1-((4-((4-methoxybenzyl)amino)-6-((4-(piperidin-1-ylmethyl)benzyl)amino)-1,3,5-triazin-2-yl)amino)imidazolidine-2,4-dione (compound 13)

Part A Preparation of 1-[4-chloro-6-(4-methoxybenzyl)amino-{1,3,5}-triazin-2-yl-amino]-imidazolidine-2,4-dione

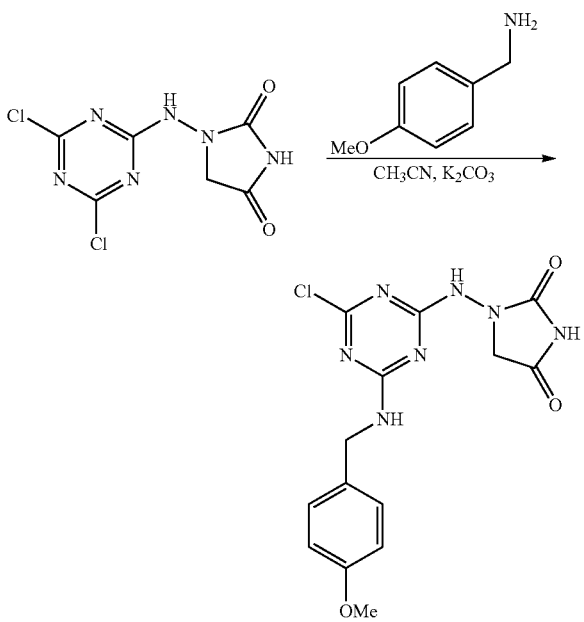

To a mixture of 1-(4,6-dichloro-[1,3,5]-triazin-2-yl-amino)-imidazolidine-2,4-dione (Example 1.1, Part A) (3.84 g, 14.6 mmol) and $K_2CO_3$ (4.4 g, 31.8 mmol) in $CH_3CN$ (50 mL) was added (4-methoxyphenyl)-methanamine (2.0 g, 14.6 mmol) drop-wise at 0° C. The mixture was stirred at r.t. overnight. TLC showed the reaction was complete. The mixture was filtered and the cake was portioned between water and EtOAc. The organic layer was separated, and the aqueous layer was extracted with EtOAc. The combined organic layers were washed with brine, dried over Na₂SO₄ and concentrated in vacuo to give the expected compound (3.50 g, yield: 66%) as a white solid. It was used for the next step without further purification. $\delta_H$ (400 MHz, DMSO-d₆): 11.30-11.23 (m, 1H), 10.06-9.83 (m, 1H), 8.67-8.60 (m, 1H), 7.24-7.13 (m, 2H), 6.90-6.83 (m, 2H), 4.40-4.35 (m, 2H), 4.26-4.05 (m, 2H), 3.73 (s, 3H). Mass spectrum (ESI) m/z 364 (100%, MH⁺).

Part B Preparation of 1-((4-((4-methoxybenzyl)amino)-6-((4-(piperidin-1-ylmethyl)benzyl)amino)-1,3,5-triazin-2-yl)amino)imidazolidine-2,4-dione (compound 13)

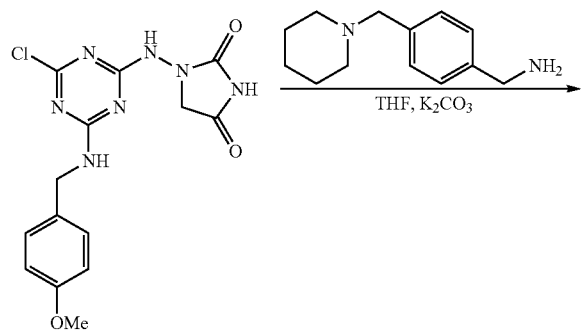

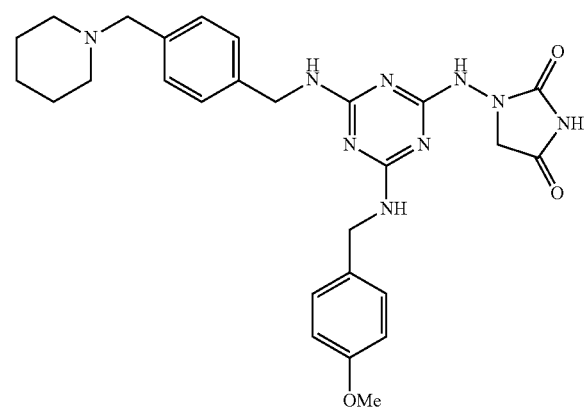 [SMILES: CCN(CC)Cc1ccc(CNc2nc(NCc3ccc(OC)cc3)nc(NN3CC(=O)NC3=O)n2)cc1]

A mixture of 1-[4-chloro-6-(4-methoxybenzyl)amino-{1,3,5}-triazin-2-yl-amino]-imidazolidine-2,4-dione (Example 1.13, Part A) (150 mg, 0.41 mmol), 4-piperidynylmethylene-benzylamine (101 mg, 0.49 mmol) and K₂CO₃ (171 mg, 1.24 mmol) in THF (8.0 mL) was heated under reflux overnight. TLC showed the reaction was complete. The mixture was cooled to r.t. and poured into water, extracted with EtOAc repeatedly. The combined organic layers were washed with brine, dried over Na₂SO₄ and concentrated in vacuo. The residue solid was purified by flash chromatography (silica gel, CH₂Cl₂: MeOH=20:1, v/v) to give compound 13 (65 mg, yield: 30%) as an off-white solid. $\delta_H$ (400 MHz, DMSO-d₆): 11.13 (br, 1H), 9.03-8.74 (m, 1H), 7.66-6.77 (m, 10H), 3.91 (s, 1H), 3.72-3.45 (m, 4H), 2.38 (s, 2H), 1.53-1.24 (m, 6H). Mass spectrum (ESI) m/z 532.3 (100%, MH⁺).

Example 1.14

Preparation of 1-((4-((4-methoxybenzyl)amino)-6-((4-(morpholino methyl)benzyl)amino)-1,3,5-triazin-2-yl)amino)imidazolidine-2,4-dione (compound 14)

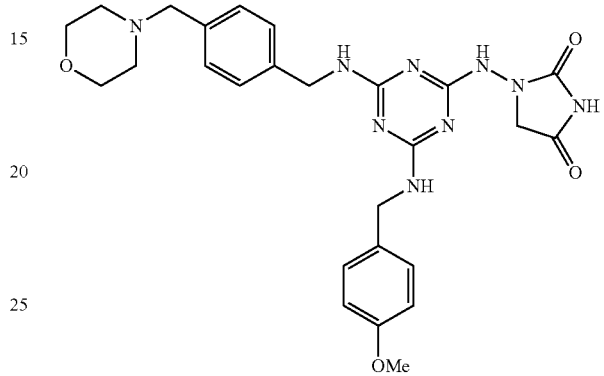

Compound 14 was produced using the synthetic procedure set out in Example 1.13, Parts A and B. $\delta_H$ (400 MHz, DMSO-d₆): 11.14-11.04 (m, 1H), 7.50-5.50 (m, 10H), 4.41-3.80 (m, 6H), 3.72 (s, 3H), 3.56 (s, 2H), 3.41 (s, 4H), 2.33 (s, 4H). Mass spectrum (ESI) m/z 534.2 (100%, MH⁺).

Example 1.15

Preparation of 1-((4-((4-((diethylamino)methyl)benzyl)amino)-6-((4-methoxybenzyl)amino)-1,3,5-triazin-2-yl)amino)imidazolidine-2,4-dione (compound 15)

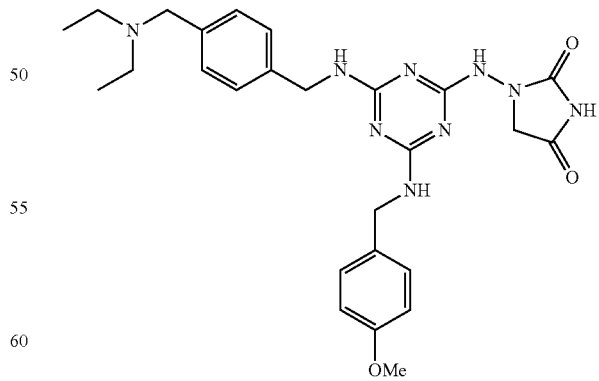

Compound 15 was produced using the synthetic procedure set out in Example 1.13, Parts A and B. $\delta_H$ (400 MHz, DMSO-d₆): 11.12-11.04 (m, 1H), 9.02-8.92 (m, 1H), 7.62-6.77 (m, 10H), 4.42-4.23 (m, 4H), 4.09, 3.92 (m, 2H), 3.72 (s, 3H), 3.53 (s, 2H), 3.55-3.52 (m, 4H), 0.99 (br s., 6H). Mass spectrum (ESI) m/z 520.3 (100%, MH+).

Example 1.16

Preparation of 1-((4-((4-methoxybenzyl)amino)-6-((4-((4-methylpiperazin-1-yl)methyl)benzyl)amino)-1,3,5-triazin-2-yl)amino)imidazolidine-2,4-dione (compound 16)

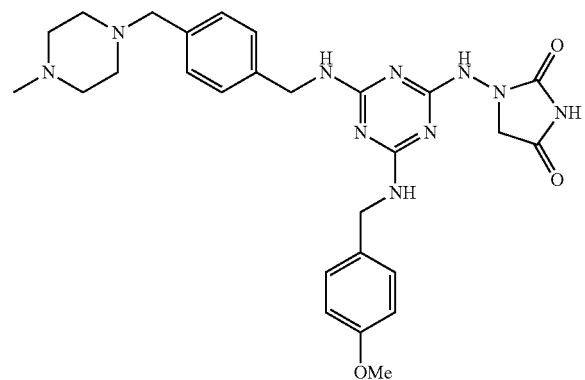 [SMILES: COc1ccc(CNc2nc(NCc3ccc(CN4CCN(C)CC4)cc3)nc(NN3CC(=O)NC3=O)n2)cc1]

Compound 16 was produced using the synthetic procedure set out in Example 1.13, Parts A and B. $\delta_H$ (400 MHz, DMSO-$d_6$): 11.07 (br s, 1H), 9.04-8.89 (m, 1H), 7.49-6.72 (m, 10H), 4.42-4.21 (m, 4H), 4.09-3.94 (m, 2H), 3.72 (s, 3H), 3.40 (s, 2H), 2.34 (br s, 8H), 1.92 (s, 3H). Mass spectrum (ESI) m/z 547.3 (100%, MH+).

Example 1.17

Preparation of 1-((4-((4-methoxybenzyl)amino)-6-((4-(piperidin-1-yl)benzyl)amino)-1,3,5-triazin-2-yl)amino)imidazolidine-2,4-dione (compound 17)

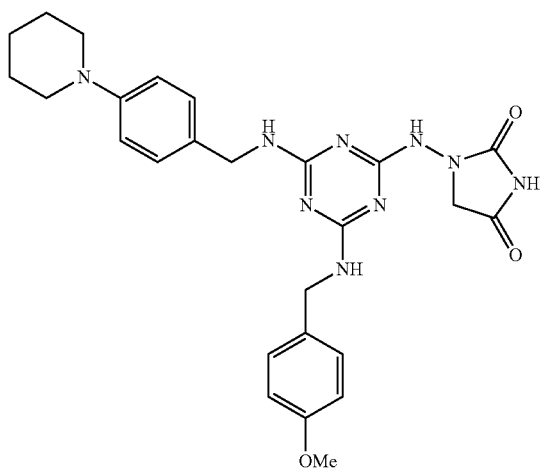 [SMILES: COc1ccc(CNc2nc(NCc3ccc(N4CCCCC4)cc3)nc(NN3CC(=O)NC3=O)n2)cc1]

Compound 17 was produced using the synthetic procedure set out in Example 1.13, Parts A and B. $\delta_H$ (400 MHz, DMSO-$d_6$): 11.14-11.03 (m, 1H), 8.90-8.70 (m, 1H), 7.56-6.84 (m, 10H), 4.35-4.02 (m, 6H), 3.72 (s, 3H), 3.07 (s, 4H), 1.60-1.51 (m, 6H). Mass spectrum (ESI) m/z 518.3 (100%, MH+).

Example 1.18

Preparation of 1-((4-((4-methoxybenzyl)amino)-6-((4-morpholino benzyl)amino)-1,3,5-triazin-2-yl)amino)imidazolidine-2,4-dione (compound 18)

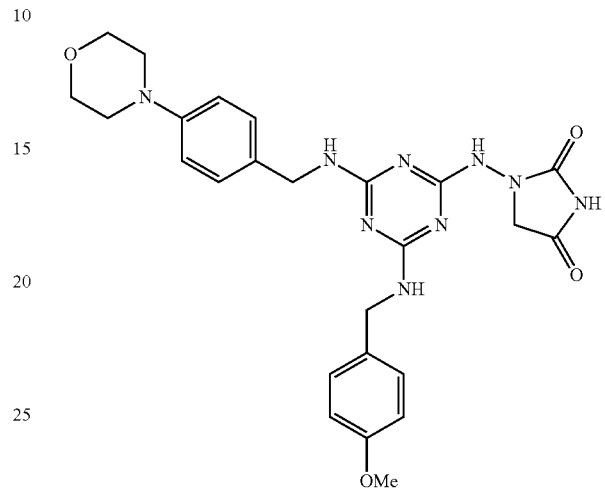

Compound 18 was produced using the synthetic procedure set out in Example 1.13, Parts A and B. $\delta_H$ (400 MHz, DMSO-$d_6$): 10.94 (br s, 1H), 8.89-8.70 (m, 1H), 7.75-6.77 (m, 10H), 4.34-4.06 (m, 6H), 3.74-3.72 (m, 7H), 3.04 (s, 4H). Mass spectrum (ESI) m/z 520.2 (100%, MH+).

Example 1.19

Preparation of 1-((4-((4-methoxybenzyl)amino)-6-((4-(4-methylpiperazin-1-yl)benzyl)amino)-1,3,5-triazin-2-yl)amino)imidazolidine-2,4-dione (compound 19)

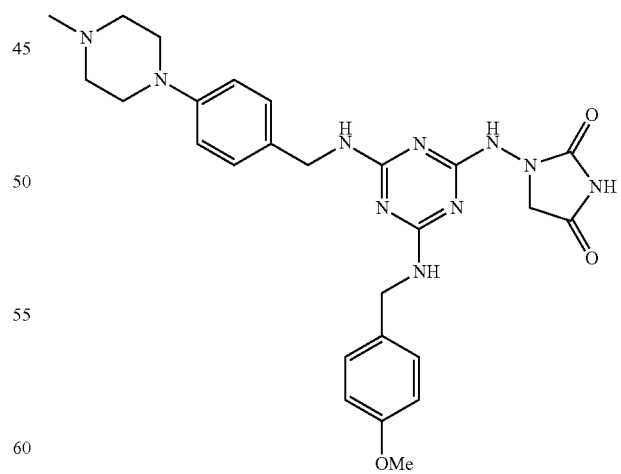

Compound 19 was produced using the synthetic procedure set out in Example 1.13, Parts A and B. $\delta_H$ (400 MHz, DMSO-$d_6$): 8.89-8.70 (m, 1H), 7.40-6.81 (m, 10H), 4.35-4.01 (m, 6H), 3.72 (s, 3H), 3.39 (br s, 4H), 3.10 (s, 4H), 2.27 (s, 3H). Mass spectrum (ESI) m/z 533.3 (100%, MH+).

Example 1.20

Preparation of 1-((4-((4-methoxybenzyl)amino)-6-((3-(piperidin-1-yl)benzyl)amino)-1,3,5-triazin-2-yl)amino)imidazolidine-2,4-dione (compound 20)

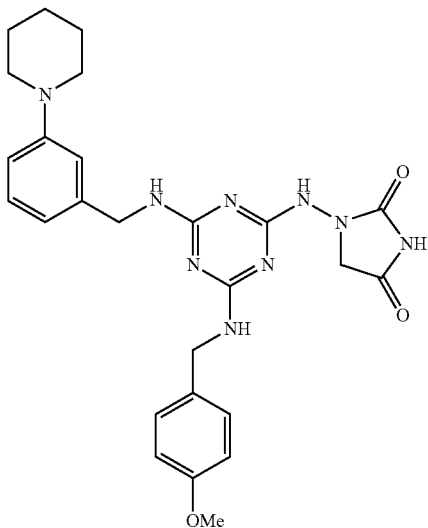 [SMILES: COc1ccc(CNc2nc(NCc3cccc(N4CCCCC4)c3)nc(NN3CC(=O)NC3=O)n2)cc1]

Compound 20 was produced using the synthetic procedure set out in Example 1.13, Parts A and B. $\delta_H$ (400 MHz, DMSO-$d_6$): 11.12-11.04 (m, 1H), 9.03-8.71 (m, 1H), 7.59-6.60 (m, 10H), 4.37-3.98 (m, 6H), 3.71 (s, 3H), 3.09 (s, 41-1), 1.59-1.51 (m, 6H). Mass spectrum (ESI) m/z 518.3 (100%, MH$^+$).

Example 1.21

Preparation of 1-((4-((4-methoxybenzyl)amino)-6-((3-morpholinobenzyl)amino)-1,3,5-triazin-2-yl)amino)imidazolidine-2,4-dione (compound 21)

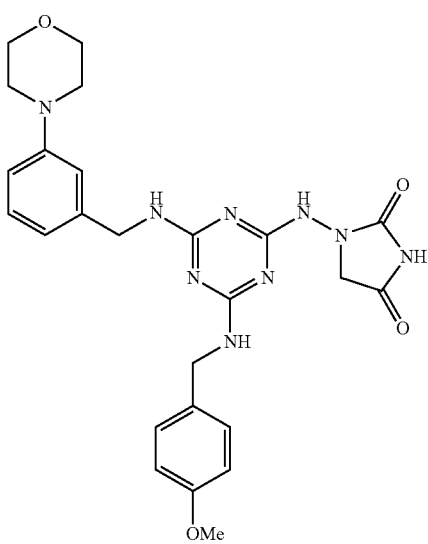 [SMILES: COc1ccc(CNc2nc(NCc3cccc(N4CCOCC4)c3)nc(NN3CC(=O)NC3=O)n2)cc1]

Compound 21 was produced using the synthetic procedure set out in Example 1.13, Parts A and B. $\delta_H$ (400 MHz, DMSO-$d_6$): 11.13-11.03 (m, 1H), 9.04-8.72 (m, 1H), 7.58-6.66 (m, 10H), 4.37-3.98 (m, 6H), 3.72 (s, 7H), 3.07 (s, 4H). Mass spectrum (ESI) m/z 520.2 (100%, MH$^+$).

Example 1.22

Preparation of 1-((4-((4-methoxybenzyl)amino)-6-((3-(4-methylpiperazin-1-yl)benzyl)amino)-1,3,5-triazin-2-yl)amino)imidazolidine-2,4-dione (compound 22)

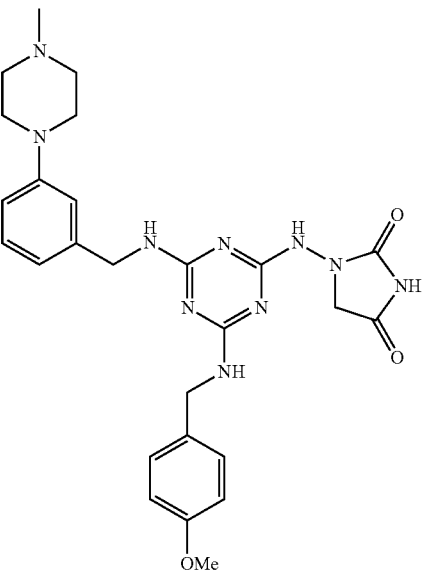 [SMILES: COc1ccc(CNc2nc(NCc3cccc(N4CCN(C)CC4)c3)nc(NN3CC(=O)NC3=O)n2)cc1]

Compound 22 was produced using the synthetic procedure set out in Example 1.13, Parts A and B. $\delta_H$ (400 MHz, DMSO-$d_6$): 11.07 (br s, 1H), 9.03-8.71 (m, 1H), 7.56-6.61 (m, 10H), 4.36-3.98 (m, 6H), 3.72 (br s, 7H), 3.12 (s, 4H), 2.27 (s, 3H). Mass spectrum (ESI) m/z 533.3 (100%, MH$^+$).

Example 1.23

Preparation of 1-((4-((4-(2-(diethylamino)ethoxy)benzyl)amino)-6-(4-methoxybenzyl)amino)-1,3,5-triazin-2-yl)amino)imidazolidine-2,4-dione (compound 23)

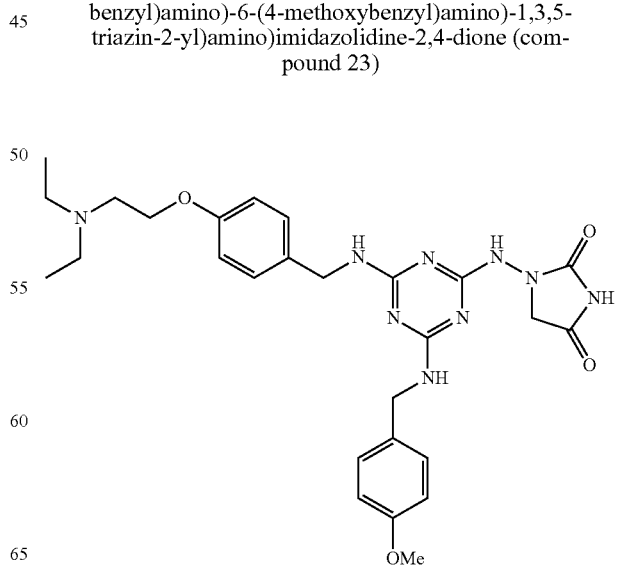

Compound 23 was produced using the synthetic procedure set out in Example 1.13, Parts A and B. $\delta_H$ (400 MHz, DMSO-$d_6$): 11.07 (br s, 1H), 9.03-8.71 (m, 1H), 7.57-6.77 (m, 10H), 4.35-3.98 (m, 8H), 3.72 (s, 3H), 2.81 (s, 2H), 2.60-2.51 (m, 4H), 0.99 (t, J=7.2 Hz, 6H). Mass spectrum (ESI) m/z 550.3 (100%, MH$^+$).

Example 1.24

Preparation of 1-((4-((4-methoxybenzyl)amino)-6-((4-(2-morpholinoethoxy)benzyl)amino)-1,3,5-triazin-2-yl)amino)imidazolidine-2,4-dione (compound 24)

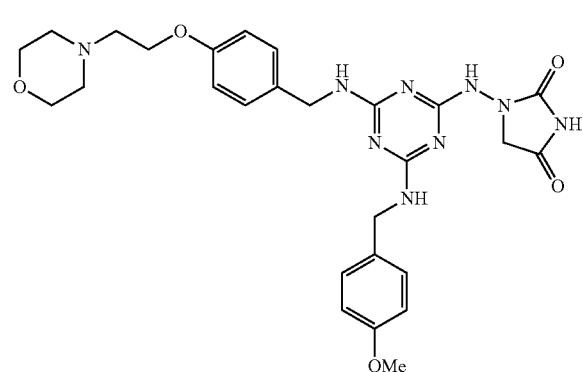 [SMILES: COc1ccc(CNc2nc(NCc3ccc(OCCN4CCOCC4)cc3)nc(NN3CC(=O)NC3=O)n2)cc1]

Compound 24 was produced using the synthetic procedure set out in Example 1.13, Parts A and B. $\delta_H$ (400 MHz, DMSO-$d_6$): 11.16-11.06 (m, 1H), 9.03-8.72 (m, 1H), 7.57-6.81 (m, 10H), 4.35-3.99 (m, 8H), 3.72 (s, 3H), 3.58 (s, 4H), 2.67 (s, 2H), 2.52-2.46 (m, 4H). Mass spectrum (ESI) m/z 564.3 (100%, MH$^+$).

Example 1.25

Preparation of 1-((4-((4-methoxybenzyl)amino)-6-((4-(2-(pyrrolidin-1-yl)ethoxy)benzyl)amino)-1,3,5-triazin-2-yl)amino)imidazolidine-2,4-dione (compound 25)

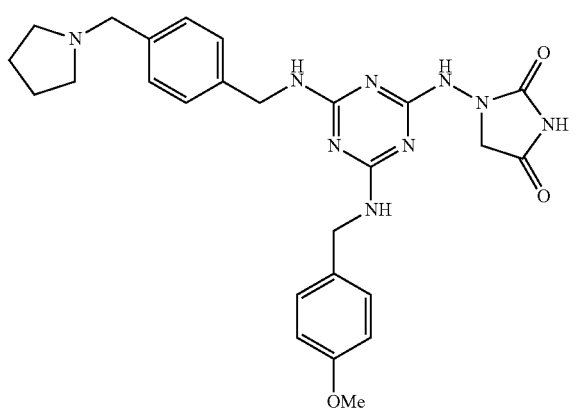 [SMILES: COc1ccc(CNc2nc(NCc3ccc(CN4CCCC4)cc3)nc(NN3CC(=O)NC3=O)n2)cc1]

Compound 25 was produced using the synthetic procedure set out in Example 1.13, Parts A and B. $\delta_H$ (400 MHz, DMSO-$d_6$): 10.78 (br s, 1H), 9.03-8.73 (m, 1H), 7.65-6.77 (m, 10H), 4.41-3.95 (m, 6H), 3.72 (s, 3H), 3.60 (s, 2H), 2.55 (br s, 4H), 1.71 (s, 4H). Mass spectrum (ESI) m/z 518.3 (100%, MH$^+$).

Example 1.26

Preparation of 1-((4-((4-methoxybenzyl)amino)-6-((4-(((2-methoxyethyl)amino)methyl)benzyl)amino)-1,3,5-triazin-2-yl)amino)imidazolidine-2,4-dione (compound 26)

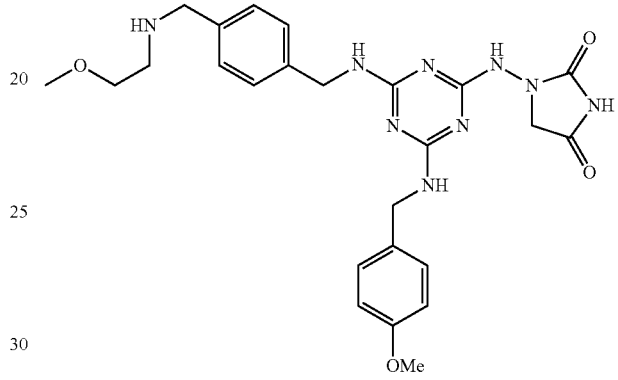

Compound 26 was produced using the synthetic procedure set out in Example 1.13, Parts A and B. $\delta_H$ (400 MHz, DMSO-$d_6$): 9.03-8.73 (m, 1H), 7.52-6.77 (m, 10H), 4.40-4.09 (m, 6H), 3.72 (s, 3H), 3.67 (s, 2H), 3.39 (m, 2H), 3.23 (s, 3H), 2.63 (s, 2H). Mass spectrum (ESI) m/z 522.2 (100%, MH$^+$).

Example 1.27

Preparation of 1-((4-((4-((dimethylamino)methyl)benzyl)amino)-6-((4-methoxybenzyl)amino)-1,3,5-triazin-2-yl)amino)imidazolidine-2,4-dione (Compound 27)

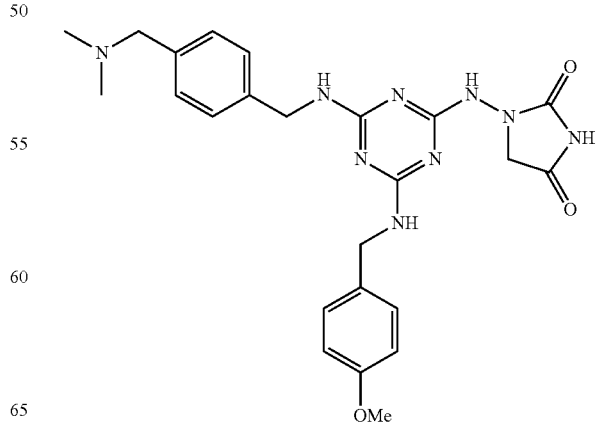

Compound 27 was produced using the synthetic procedure set out in Example 1.13, Parts A and B. $\delta_H$ (400 MHz, DMSO-$d_6$): 11.07 (br s, 1H), 9.04-8.75 (m, 1H), 7.66-6.74 (m, 10H), 4.44-3.91 (m, 6H), 3.72 (s, 5H), 2.34 (s, 6H). Mass spectrum (ESI) m/z 492.2 (100%, MH+).

Example 1.28

Preparation of 1-((4-((4-methoxybenzyl)amino)-6-((4-(piperazin-1-ylmethyl)benzyl)amino)-1,3,5-triazin-2-yl)amino)imidazolidine-2,4-dione 2,2,2-trifluoroacetate (compound 28)

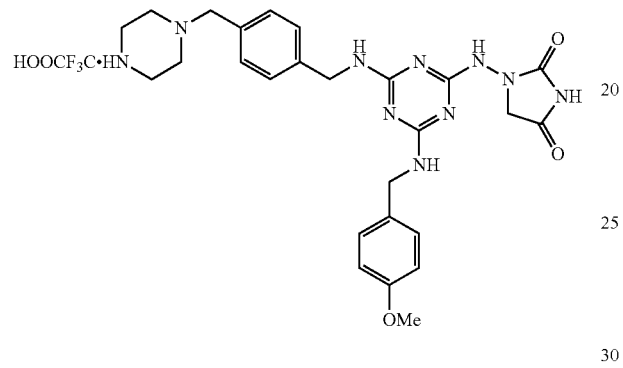

Compound 28 was obtained by deprotection of the corresponding Boc-protected 4-(piperazin-1-ylmethyl)benzyl) amino derivative which was produced using the synthetic procedure set out in Example 1.13, Parts A and B. $\delta_H$ (400 MHz, CD$_3$OD): 7.42-6.83 (m, 8H), 4.64-4.47 (m, 4H), 4.20-3.93 (m, 4H), 3.79 (s, 3H), 3.34-3.32 (m, 4H), 3.12-3.01 (m, 4H). Mass spectrum (ESI) m/z 533.3 (100%, MH+).

Example 1.29

Preparation of tert-butyl 4-(((4-((2,4-dioxoimidazolidin-1-yl)amino)-6-((4-methoxybenzyl)amino)-1,3,5-triazin-2-yl)amino)methyl)benzylcarbamate (compound 29)

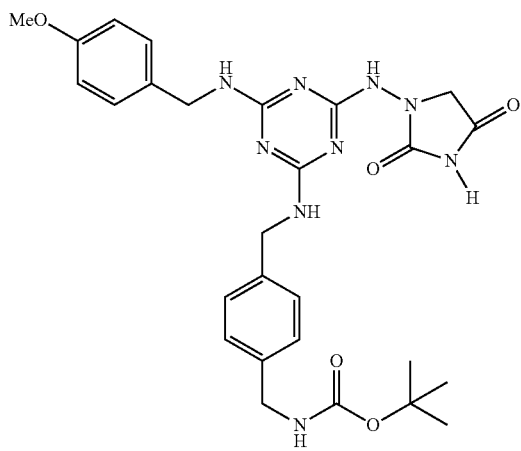 [SMILES: COc1ccc(CNc2nc(NCc3ccc(CNC(=O)OC(C)(C)C)cc3)nc(NN3CC(=O)NC3=O)n2)cc1]

Compound 29 was produced using the synthetic procedure set out in Example 1.4, Parts A and B using 1-(4,6-dichloro-[1,3,5]-triazin-2-yl-amino)-imidazolidine-2,4-dione (Example 1.1, Part A) as the starting material.

Example 1.30

Preparation of 5-((4,6-bis((4-hydroxybenzyl)amino)-1,3,5-triazin-2-yl)amino)-3-methylimidazolidine-2,4-dione (compound 30)

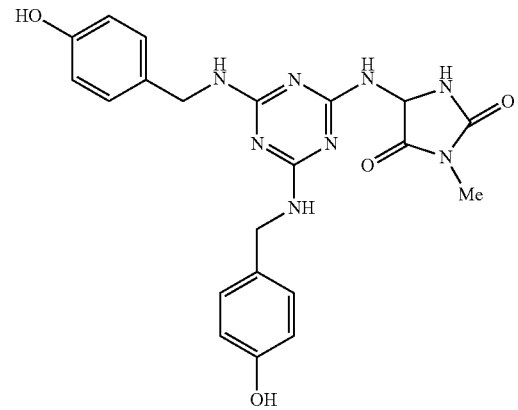 [SMILES: CN1C(=O)NC(Nc2nc(NCc3ccc(O)cc3)nc(NCc3ccc(O)cc3)n2)C1=O]

Compound 30 was produced adapting the synthetic procedures described above.

Example 2

Biological Testing

Example 2.1

Inhibition of Proliferation and Duration of Inhibition in Cancer Cell Lines

Triazine compounds of the present invention have been shown to block the cell cycle at G2/M. Triazines were tested for their inhibitory activity on the "in vitro" growth of tumor cell lines. For the initial studies two colon carcinoma cell lines (LIM1215 and SW480) and two breast cancer cell lines (MDA-MB-231 and MCF-7) were used. Taxol was used as comparator in these experiments (Table 1).

All triazines tested were at least as effective as Taxol in inducing G2/M block at their optimal concentration (Table 1).

TABLE 1

Antimitotic effects of triazines on carcinoma cell lines. Inhibitors were added to cells in log-growth for a period of 24 hrs. Cell cycle phase distribution was monitored by DNA staining and analysis in ModFit.

| Inhibitor | LIM1215 | | SW480 | | MDA-MB-231 | | MCF-7 | |
|---|---|---|---|---|---|---|---|---|
| | $IC_{50}$[a] (µM) | % of Taxol[b] | $IC_{50}$[a] (µM) | % of Taxol[b] | $IC_{50}$[a] (µM) | % of Taxol[b] | $IC_{50}$[a] (µM) | % of Taxol[b] |
| Taxol | 0.01 | 100 | 0.008 | 100 | 0.008 | 100 | 0.008 | 100 |
| Compound 3 | 3 | 108 | 1.45 | 106 | 3 | 93 | 0.45 | 102 |
| Compound 1 | 0.07 | 105 | 0.05 | 120 | 0.013 | 94 | 0.009 | 108 |
| Compound 2 | NT | NT | 0.25 | 113 | 0.009 | 103 | 0.009 | 102 |

[a]$IC_{50}$, for progression through the cell cycle and
[b]the proportion of cells in G2/M after exposure to 1 µM Taxol was used as a standard; triazine potency is expressed as proportion of cells in G2M (test)/proportion of cells in G2M (Taxol).
The maximum number of cells in G2/M in these experiment were: LIM1215 = 78.5%; SW480 = 72%; MDA-MB-231 = 55%; MCF-7 = 62%.
NT = not tested.

Example 2.2

Effects of Triazines on Cancer Cell Growth "In Vitro"

The inhibition of proliferation was also measured in a panel of tumor cell lines by the MTT assay (General Protocol see Example 2.6). The $IC_{50}$ determined by this assay which measures cell proliferation matched closely the values calculated from FACS analysis of G2/M block, indicating that the G2/M arrest does indeed prevent cell proliferation. Wash-out experiments after incubation of the cells with the drug resulted in resumption of proliferation in breast cancer cell lines, and complete arrest in one colorectal carcinoma cell line, suggesting that the drug is cytotoxic in at least some cell types.

Example 2.3.1

Biological Effects of Triazines on Tumor Cell Growth

Compound 2 was tested on a series of cell lines to determine its activity and selectivity (Table 2). Cell proliferation was measured using the MTT assay (for protocol see Example 2.6) after 3 days of incubation with the inhibitor.

TABLE 2

Inhibition of proliferation of tumor cell lines by compound 2: [a]murine B-cell progenitor line; [b]human colorectal carcinoma; and [c]human breast carcinoma.

| Cell line | $IC_{50}$ (µM) |
|---|---|
| BaF/3[a] | 0.03 |
| LIM 1215[b] | 0.09 |
| LIM 2537[b] | 0.07 |
| LIM 2405[b] | 0.03 |
| SW 480[b] | 0.03 |
| MDA-MB-231[c] | 0.01 |
| MCF-7[c] | 0.01 |

The $IC_{50}$ for the different cell lines were very similar, suggesting that compound 2 targets a common pathway necessary for completion of G2/M.

Example 2.3.2

Effects of the Triazines on Tubulin Polymerization Both 'In Vitro' and 'In Vivo'

The effects of the triazines on tubulin polymerization both 'in vitro' and 'in vivo' were tested. These experiments showed that triazine-induced tubulin polymerization was minimal and occurred at doses far exceeding the drug potency as a mitotic blocker.

To monitor the effects of triazines on tubulin, the present inventors tested tubulin polymerization in intact cells following exposure to the drug.

Cells treated with Taxol or with compound 3 were lysed in hypotonic buffer containing 0.5% NP-40 and the cellular extracts were centrifuged at high speed. Polymerized tubulin is detergent-insoluble: thus after this treatment soluble tubulin is recovered in the supernatants (S), and polymerized tubulin in the cellular pellets (P). The relative proportion of the two forms was monitored by SDS/PAGE and immunoblotting with tubulin-specific antibodies.

In this test, Taxol strongly stabilized tubulin in a dose-dependent manner while the triazines showed negligible effects even at high concentrations (FIG. 1).

Figure 2:
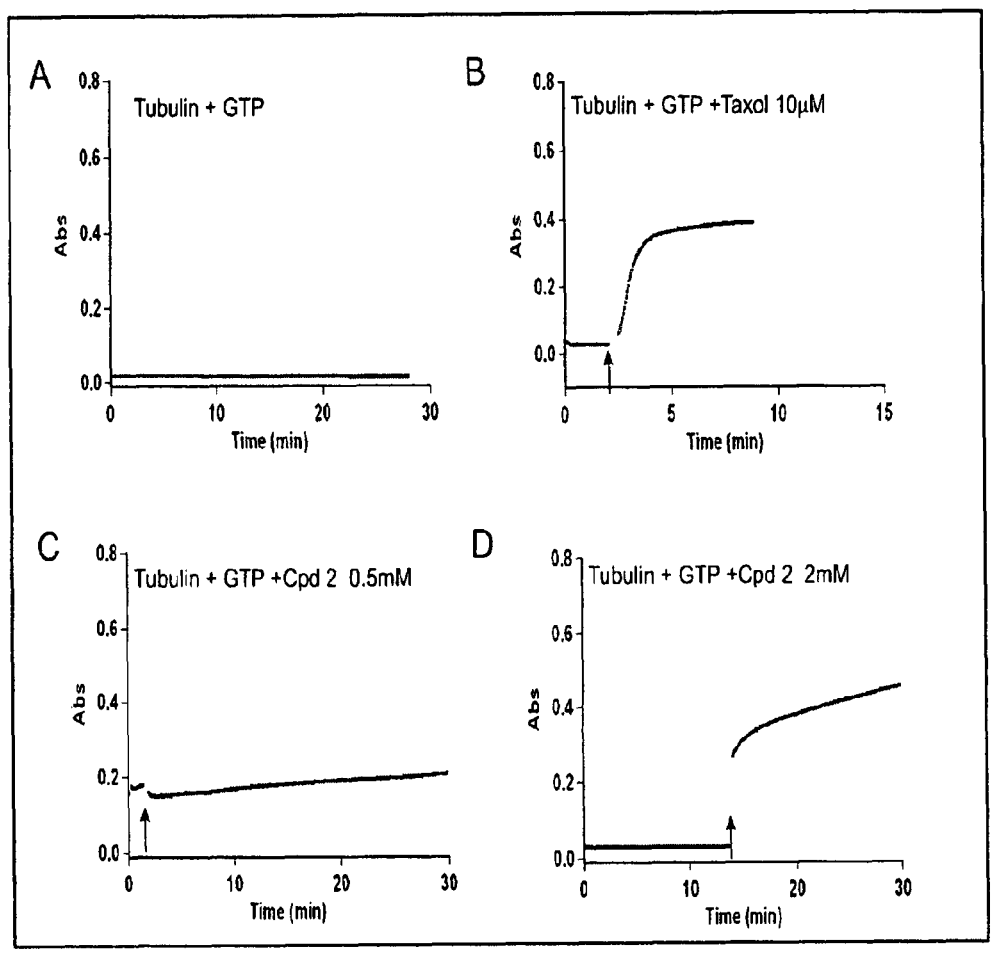
FIG. 2: Effect of compounds of the present invention on "in vitro" tubulin polymerization. Tubulin (1 mg/ml in PIPES/MgCl$_2$/GTP buffer) was pre-equilibrated in the cuvette of a Cary 50 spectrophotometer before addition of buffer (A), Taxol (B), 0.5 mM triazine (C) or 2 mM triazine (D), (arrow). OD[340] readings were taken at 5 s intervals for 30 min.

In an attempt to examine direct interactions of the triazines with tubulin, 'in vitro' tubulin polymerization assays were used (FIG. 2). In these assays the triazines caused a small but significant increase in tubulin polymerization. However, the concentration of triazine required for tubulin polymerization was more than 1,000 times greater than the $IC_{50}$ in cell proliferation assays.

Example 2.3.4

Dose Escalation in Mice

Compound 1 was initially tested for tolerability and toxicity in mice. C57Bl/6 mice (aged 8-12 weeks) were injected subcutaneously with escalating doses of Compound 1 in a constant volume of DMSO. Mice were sacrificed 24 hrs post-injection. There were no adverse effects of doses up to 80 mg/kg within this time-frame. Thus the compound is well tolerated at doses that far exceed the $IC_{50}$ observed "in vitro".

Compound 2 showed no adverse effects in outward health or behaviour from doses up to 64.5 mg/kg for 4 days. At 21.5 and 64.5 mg/kg there were indications of skin thinning at the injection site in some mice. In BALB/c nude mice Compound 2 caused some skin lesions at 20 mg/kg. These minor skin lesions healed readily within 2-3 days.

Example 2.4

Pharmacokinetics

The pharmacokinetic parameters for Compound 2 were determined following injection into mice.

When delivered at a dose of 50 mg/kg in aqueous solution, the drug reaches plateau concentrations in the blood stream of 60 μM and remains at levels of up to 6 μM for 6-10 hours. The elimination half-life is approximately 1.5 hr. At least two active metabolites, inducing G2/M cell cycle block 'in vitro', have also been detected in the plasma, and their structures confirmed by mass spectrometry. When the active metabolites are included in the pharmacokinetic calculations, the total concentration of the active drug averages 30 μM for up to 6 hours before it begins to be eliminated from the plasma.

Example 2.4.1

Extraction and Quantitation of Triazines from Mouse Blood

The protocol developed for the extraction of active triazines from mouse plasma and RP-HPLC quantitation of the extracted drug, as well as the characterization of the metabolites and the pharmacokinetic properties of the compounds, is described below.

Example 2.4.1.1

Extraction of Triazines from Mouse Plasma

Mouse blood was collected by cardiac puncture after anaesthesia by $CO_2$ gas. Mice were subsequently euthanized. The blood was transferred to an EDTA tube to prevent clotting and the plasma collected after separation by centrifugation. For each sample 25 μl plasma was added to 75 μl cold 0.1% TFA (v/v) with 5 μM hydrocortisone (HC) as an internal standard. These processed samples were stored at −20° C. until required. On thawing they were clarified by centrifugation and the extracts were analyzed on RP-HPLC.

Example 2.4.1.2

Quantitation of Triazines in Mouse Plasma

Figure 3:
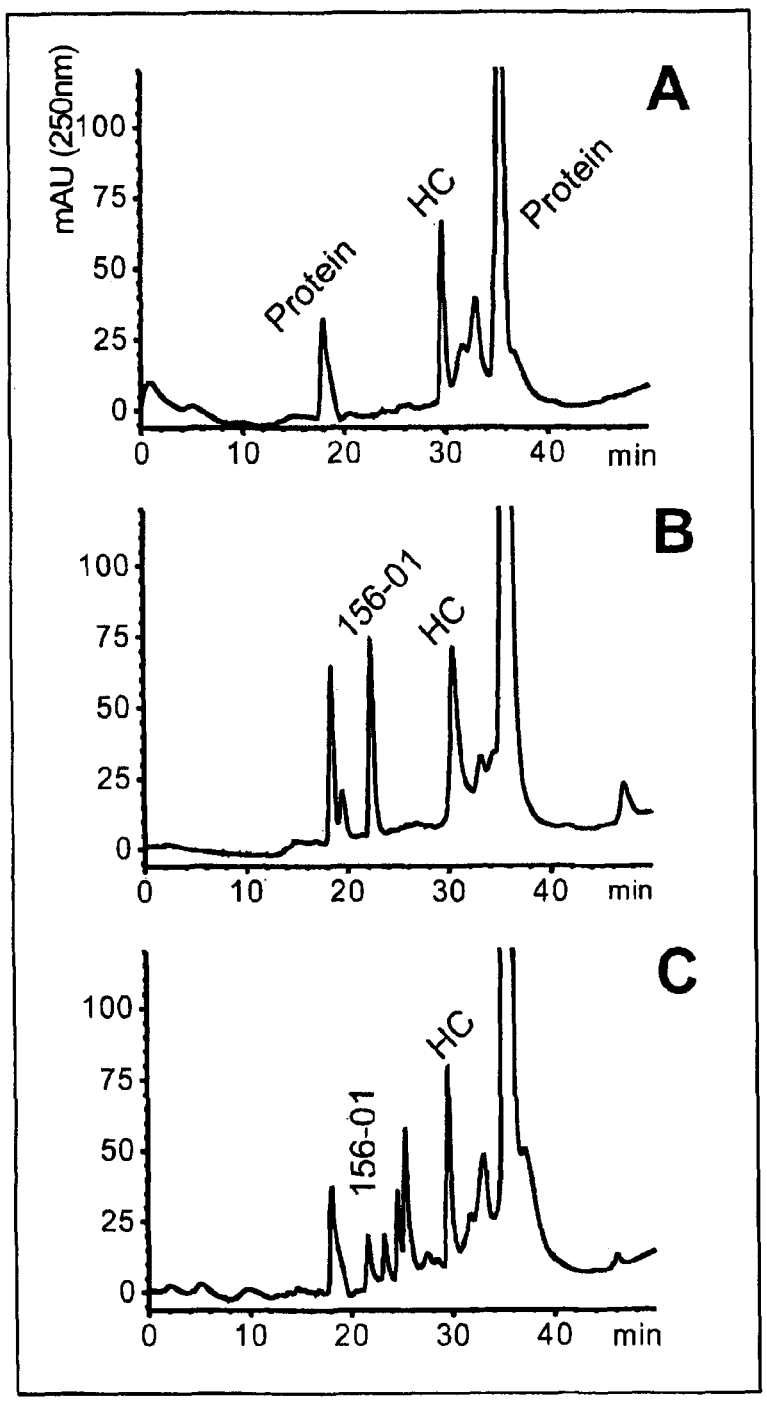
FIG. 3: Representative chromatograms of extracted mouse plasma. A: Normal mouse plasma with HC. B: Normal mouse plasma spiked with Compound 2 (156-01) and HC for, the standard curve. C: Plasma obtained 2 hours after injection of Compound 2 (156-01) shows the recovered Compound 2 (156-01) peak as well as 3 other putative metabolite peaks.

Each 100 μl plasma extract was separated on a Zorbax SB-C18, 2.1×150 mm, 5μ column using a linear 50 min gradient of acetonitrile in 0.1% (v/v) TFA at a flow rate of 0.1 ml per minute and a column temperature of 45° C. Detection was at 250 nm. Representative chromatograms are shown in FIG. 3.

Example 2.4.1.3

Analysis of Compound 2 Metabolites

Chromatograms of plasma from mice injected with compound 2, but not from control mice, contained minor peaks. These peaks appeared at a later time after injection of compound 2, and are presumably metabolites. In order to confirm the identity of these peaks, their absorption spectra were compared with that of the compound 2 standard.

Figure 4:
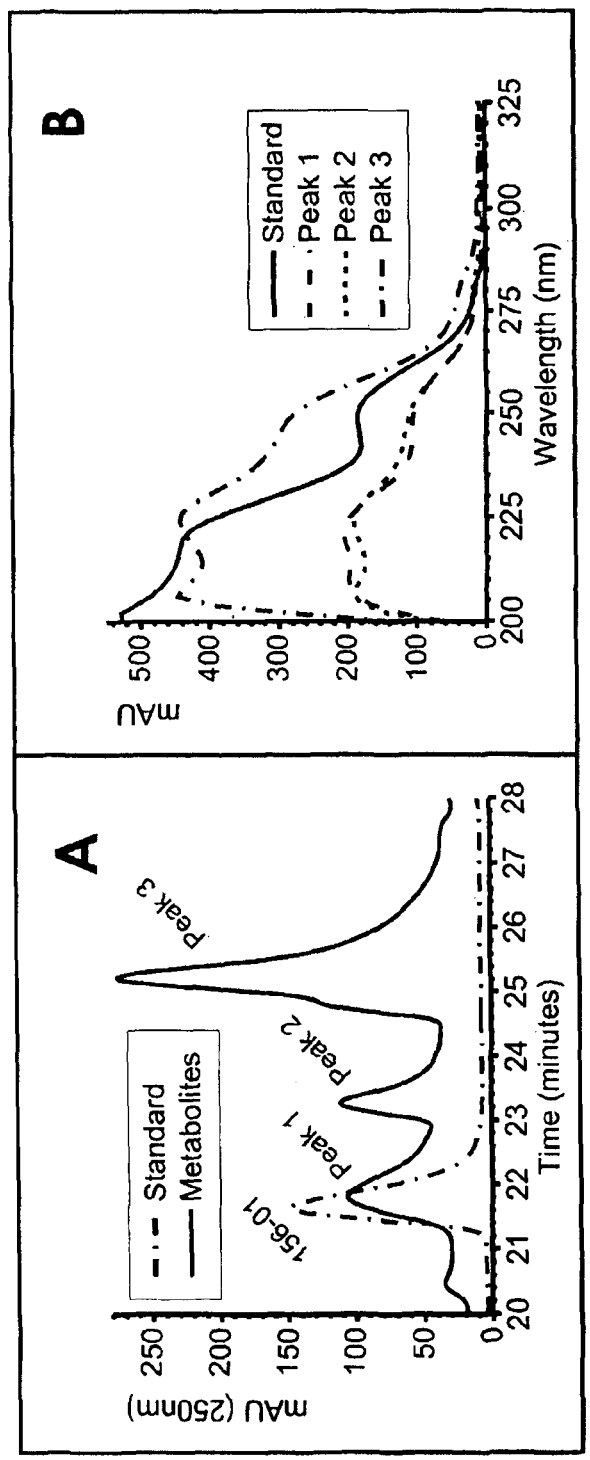
FIG. 4: Spectral analysis of putative metabolite peaks. A. Overlaid chromatograms of standard compound 2 (156-01) in plasma (dotted line) and the plasma of an injected mouse (solid line). B. UV spectra of the purified peaks.
Figure 5:
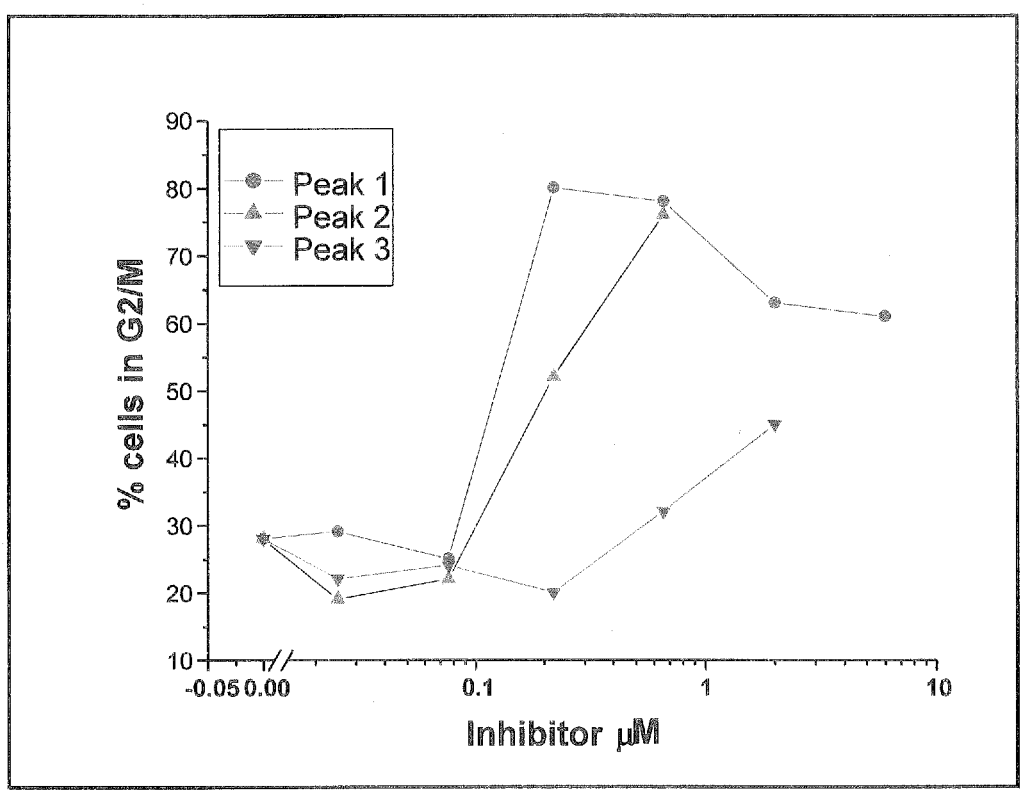
FIG. 5: Anti-mitotic effects of metabolites recovered from mouse plasma after compound 2 injection. BaF/3 cells were incubated for 24 hr with increasing amounts of each reconstituted peak. Cell cycle distribution was assessed by FACS analysis using Propidium Iodide. The percentage of cells in the G2/M phase of the cell cycle was determined using ModFi

As can be seen in FIG. 4, all of the peaks had the characteristic 250 nm absorbance and appear to be related compounds. The mouse plasma was fractionated on RP-HPLC and the peaks indicated above were collected. The pooled peak samples were concentrated by lyophilization. A portion of each peak sample was reconstituted in culture media for bioassay (FIG. 5). The remainder was analyzed by LC-MS to confirm the mass and identify the structures.

The $IC_{50}$ for recovered compound 2 (Peak 1), Peak 2 and Peak 3 were 0.1 μM, 0.2 μM and >1 μM, respectively. Although it was difficult to quantify exactly the concentration of the recovered peaks because of the very small amounts, the assay does indicate that all recovered peaks had some biological activity.

The results of LC-MS analysis of the recovered compounds are shown in Table 3.

TABLE 3

| Results of LC-MS analysis of metabolites recovered from mouse plasma after compound 2 injection. | |
| --- | --- |
| Sample | Mass (Da) |
| Compound 2 | 464.2 (M + 1) |
| Peak 1 | 464.1 (M + 1) |
| Peak 2 | 655.0 (M + 1) |
| Peak 3 | 479.1 (M + 1) |

Analysis of the starting material compound 2 confirmed the molecular weight of the free base compound to be 464 Da. Peak 1 had the same mass which confirmed that it is the same compound recovered from the plasma. Peak 3 had a mass of 479 Da suggesting a hydroxyl derivative. Peak 2 was a much larger compound with a mass of 655 Da. The additional mass indicates that it is a glucuronide derivative of the hydroxyl derivative.

These results confirm that the recovered compounds are active metabolites of compound 2 and should be included in the calculations of active levels of drug in plasma and the elimination half-life of the compound.

Example 2.4.1.4

Pharmacokinetic Analysis of Compound 2

Figure 6:
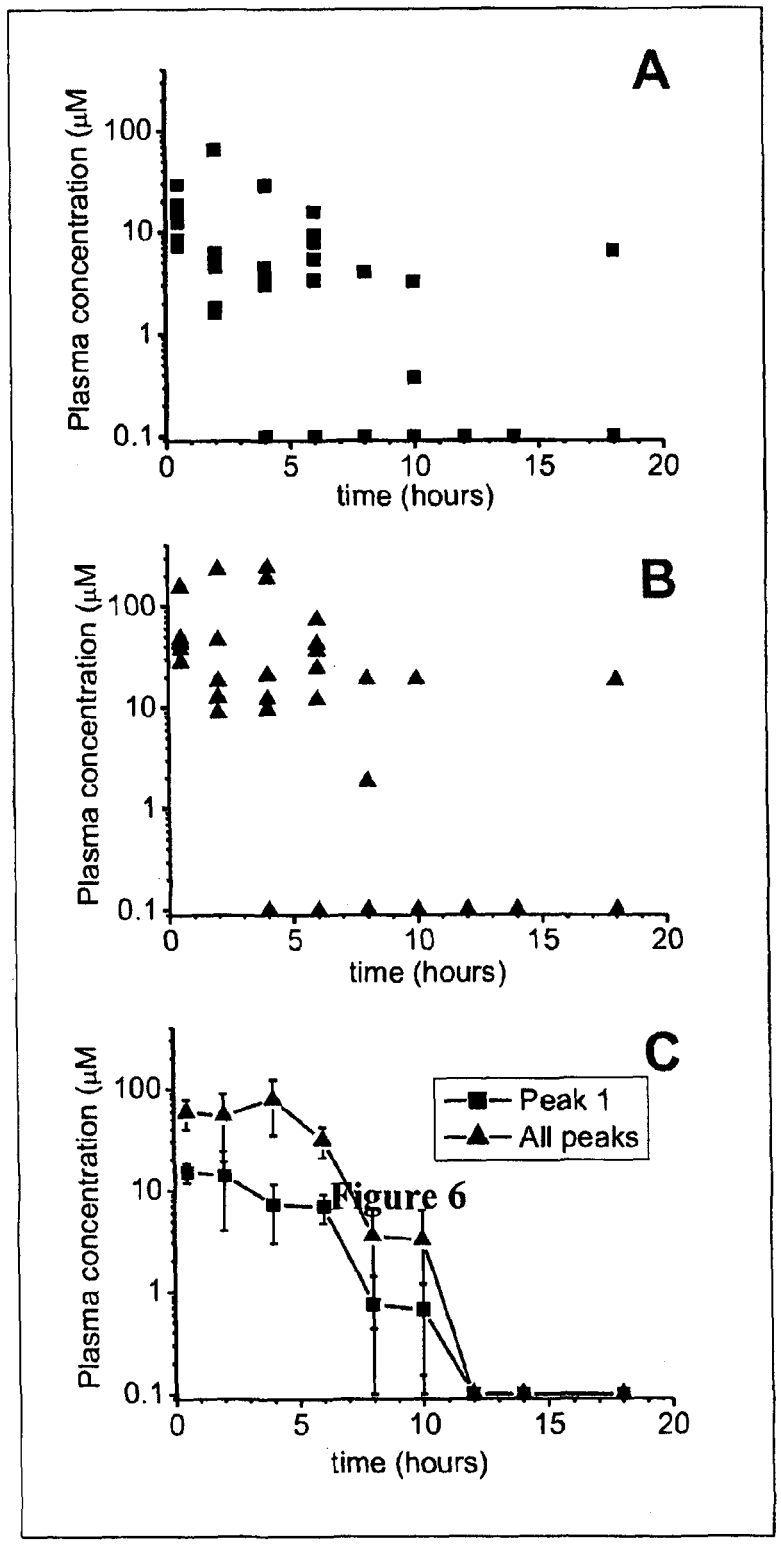
FIG. 6: Plots of plasma concentrations of compound 2 in mice following a single subcutaneous dose of 50 mg/kg. Each point corresponds to an individual mouse. A: Semi-log plot of calculated concentrations of Peak 1 values. B: Semi-log plot of values including all metabolite peaks. C: Mean and se values comparing Peak 1 only with all peaks.

The concentration of drug in the plasma was determined by the internal standard method of calibration by comparing the ratios of drug to HC peak areas relative to the known standards. Plasma concentrations of compound 2 in the mice from one pharmacokinetics experiment are plotted in FIG. 6

These results suggest that therapeutically significant concentrations of compound 2 can be achieved in the serum, and maintained for up to 10 hr.

Example 2.5

Efficacy as Anti-Tumor Drug in Xenograft Experiments

Xenograft experiments have been used to determine the efficacy of compound 2 in reducing tumor growth. In initial experiments, using the established tumor model with the colorectal carcinoma cell line LIM 2537, compound 2 has significantly reduced the rate of growth of the tumors.

Example 2.5.1

Tumor Xenograft Studies with LIM 2537 Cells (Colon Carcinoma Cell Line)

Method:

The colon carcinoma cell line LIM 2537 was chosen for tumor xenograft studies in BALB/c nude mice, as its growth was shown to be inhibited by compound 2 (see "Biological effects of triazines on tumor cell growth").

The mice were inoculated with $3 \times 10^6$ cells per tumor in 100 µl PBS, one tumor on each flank subcutaneously (SC). Treatments were started on the third day after inoculation with either vehicle control (VC) or 100 µl of drug at 3 mg/ml in aqueous solution giving a dose of 15 mg/kg. Mice were injected SC in the abdomen, three times per week for the duration of the experiment. The mice were monitored for body weight, tumor volume and appearance, and for any adverse reactions to the drug. The experiment was terminated after 33 days and the control group euthanized, as the tumor burden in that group had reached the maximum allowed. The remaining mice were then left without treatment for a further 9 days to monitor resumption of tumor growth.

Figure 7:
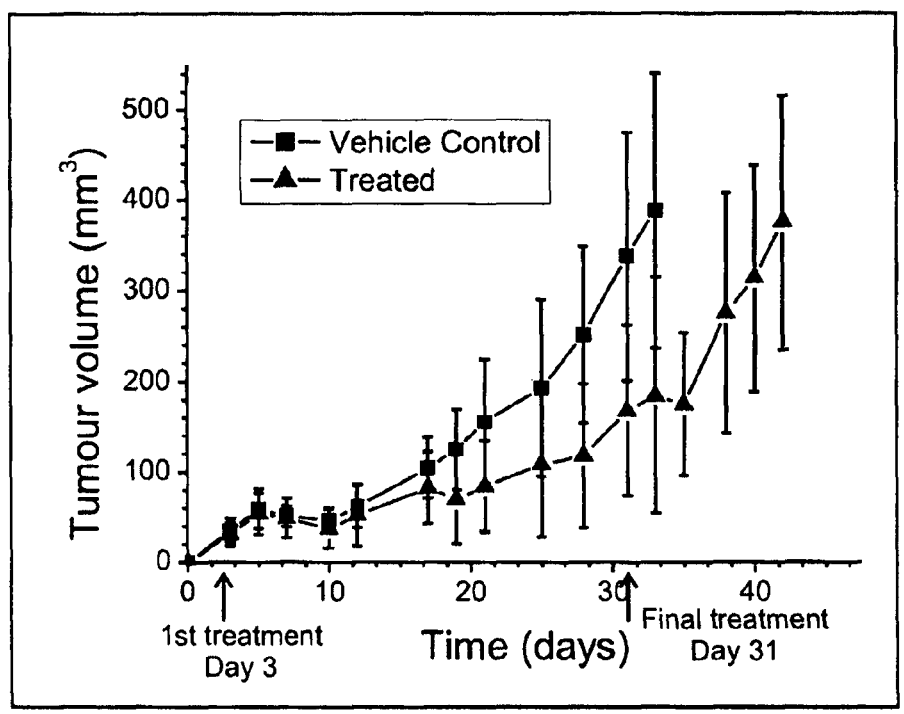
FIG. 7: LIM2537 tumor growth in nude mice. Tumor diameters were measured with external callipers every three days and tumor volume calculated with the formula: $\pi/6\times(L\times W^2)$. Clear difference between vehicle control treated animals (black curve) and those treated with compound 2 (red curve) at 15 mg/kg, three days a week starting on day 3 of the experiment.

Results:

Mouse body weights were not affected by the drug treatment. Differences in tumor size between control and drug groups were apparent after 12 days, and by the $33^{rd}$ day, when the control group was euthanized, this difference was distinct. Within the groups, there was one slowly growing tumor in the controls and one fast-growing tumor in the treated cohort. These anomalous tumors are responsible for the large standard deviations (FIG. 7).

From this experiment it can be concluded that the treatment schedule (3 injections per week of compound 2 at a dose of 15 mg/kg) was successful in slowing the growth of LIM 2537 cells. There was no long term adverse reaction to the drug at this dose and formulation.

Example 2.5.2

Tumor Xenograft Studies with U87MG(Δ2-7)—(Brain Cancer Cell Line)

Method:

Mice: Balb/c nu/nu male; 8 controls and 8 treated.

Cells inoculated: U87MG(Δ2-7) at $2.13 \times 10^6$ cells/tumour; two tumours per mouse.

Dose: Compound 2 at 20 mg/kg=100 µl of 4 mg/ml in water for injection per 20 g mouse. Control mice were injected with 100 µl water for injection.

Treatment and monitoring: Treatment commenced at Day 5 after inoculation. Mice were injected SC in abdomen three times per week (Mon, Wed, Fri), on alternating sides. Mice were weighed, tumour diameters measured in two dimensions and the health of the mice was monitored.

After mice were sacrificed: the tumours were dissected and weighed; spleens and livers were also weighed.

Figure 8:
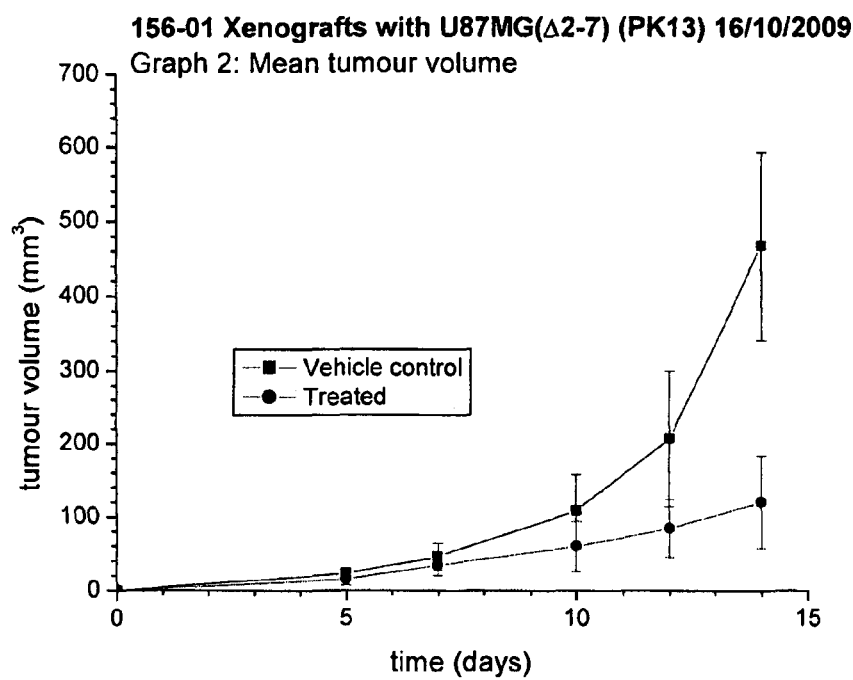
FIG. 8: U87MG(Δ2-7) tumor growth in nude mice. Tumor diameters were measured with external callipers every three days and tumor volume calculated with the formula: $\pi/6\times(L\times W^2)$. Clear difference between vehicle control treated animals (black curve) and those treated with compound 2 at 20 mg/kg, three times a week starting on day 5 of the experiment.

Results:

The tumours grew rapidly and consistently between animals. The experiment was terminated at 14 days after inoculation because most of the control mice had reached maximum tumour burden, and some tumours were beginning to ulcerate. At the end of the experiment there was a significant difference in volume between control and treated tumours (FIG. 8).

Figure 9:
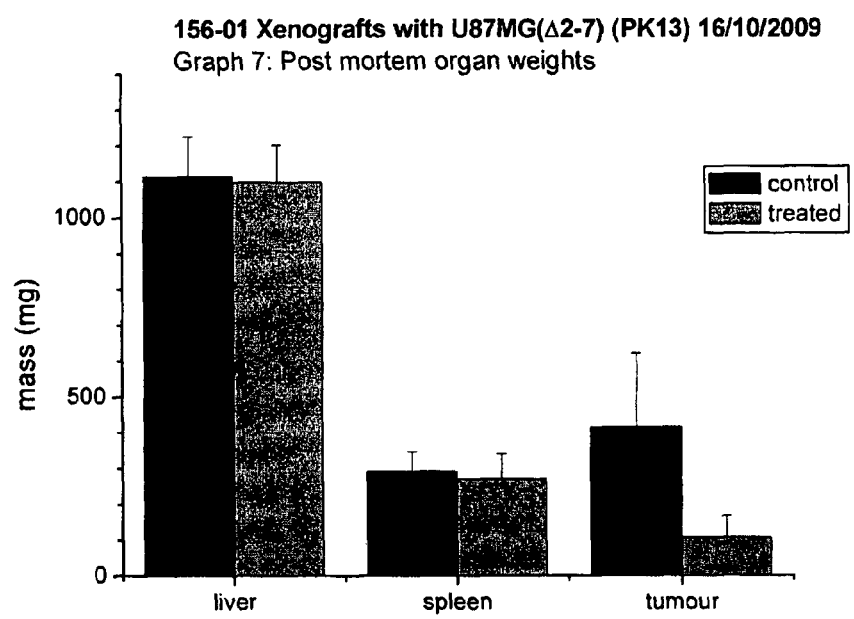
FIG. 9: Animals treated with compound 2 (labelled "156-01") (green bars) showed no significant difference in their liver or spleen weights from vehicle control treated animals (red) whereas the tumor weight was greatly reduced.

Livers and spleens were also weighed post mortem. In FIG. 9 the mean weights of these organs are compared, together with the mean weights of the tumours.

Treatment of U87MG(Δ2-7) tumours with compound 2 at 20 mg/kg three times per week has reduced the growth of the tumours compared with tumours in vehicle control injected mice.

Example 2.5.3

Tumor Xenograft Studies with H1437 (Non-Small Cell Lung Cancer Line)

Method:

Mice: Balb/c nu/nu male; 8 controls and 8 treated; 5 weeks old.

Cells inoculated: H1437 (non-small cell lung cancer cell line) at $2 \times 10^6$ cells/tumour; two tumours per mouse.

Dose: Compound 2 at 20 mg/kg=100 µl of 4 mg/ml in water for injection per 20 g mouse. Control mice were injected with 100 µl water for injection.

Treatment and monitoring: Treatment commenced at Day 5 after inoculation. Mice were injected SC in abdomen three times per week, on alternating sides. Mice were weighed; tumour diameters measured in two dimensions and the health of the mice was monitored. Injections correspond to data points on the plots, with an additional treatment on Day 14 when no measurements were made.

Figure 10:
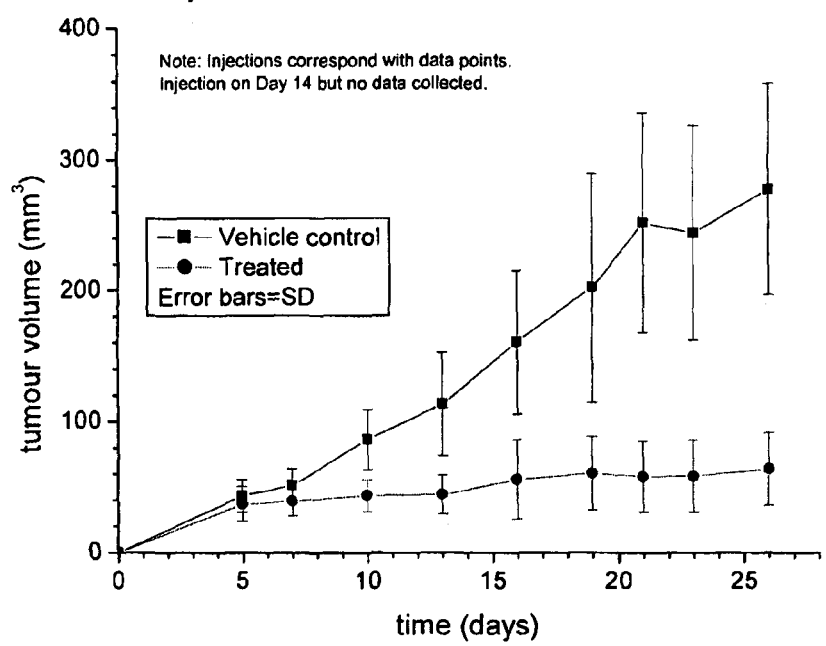
FIG. 10: H1437 tumor growth in nude mice. Tumor diameters were measured with external callipers every three days and tumor volume calculated with the formula: $\pi/6\times(L\times W^2)$. Clear difference between vehicle control treated animals (black curve) and those treated with compound 2 at 20 mg/kg, three times a week starting on day 5 of experiment.

Results:

The tumours in the control group grew rapidly but with some variation between animals. The measured volume of the tumours stabilized after 21 days, and the growth rate did not increase as it had with cell lines in previous experiments. These tumours generally grew as high round balls rather than spreading along the flank of the animal. The experiment was terminated at 26 days after inoculation because most of the control mice had reached maximum tumour burden. There was no ulceration of the tumours which remained under the skin and did not appear particularly vascularised. In contrast, the tumours in the treated group remained very small and hard throughout the 26 days. At the end of the experiment there was a significant difference in volume between control and treated tumours (FIG. 10).

Figure 11:
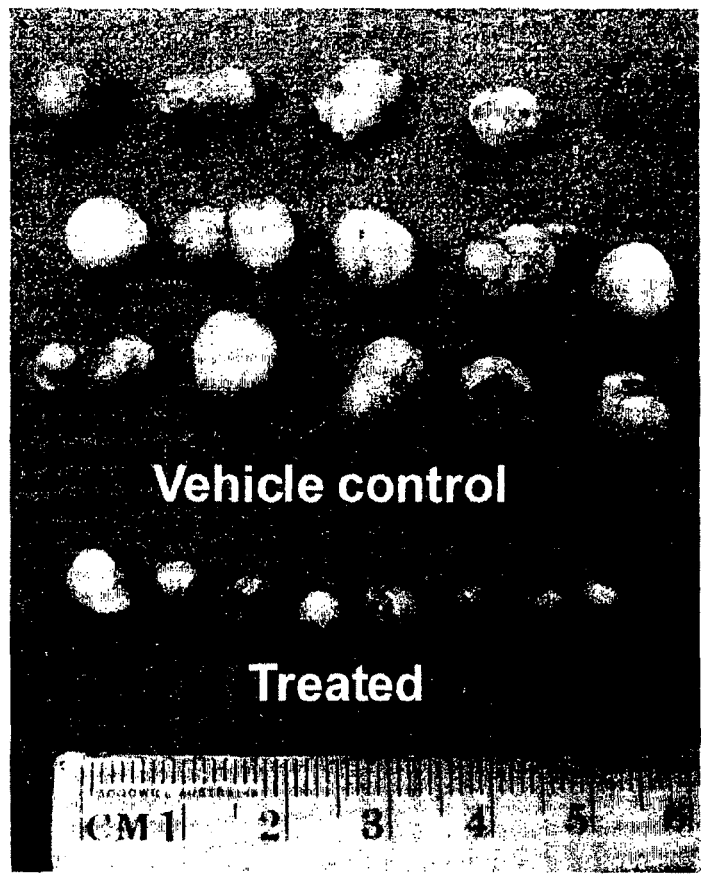
FIG. 11: Photograph of the H1437 xenograft tumors removed from the vehicle control treated animal (top three rows) and compound 2 treated (20 mg/kg, three times per week) bottom row. A clear difference in size can be seen.

After the mice were sacrificed the tumours were dissected and weighed. After dissection the tumours from the two groups were compared. There is a striking difference in the observed size of the tumours between the two groups (FIG. 11).

It will be appreciated by persons skilled in the art that numerous variations and/or modifications may be made to the invention as shown in the specific embodiments without departing from the scope of the invention as broadly described. The present embodiments are, therefore, to be considered in all respects as illustrative and not restrictive.

Example 2.6

Protocol for MTT and MTS Assay for all Cells and Inhibitors

Example 2.6.1

General Summary

Cells plated at 104/well in 100 µl medium+5% FCS(+Adds[1]):
Cells incubated overnight:
Titrate inhibitors in a fresh plate in 150 µl medium
Transfer 100 µl titrated compounds to matching wells of the cell plate.

Incubate a further 4 days:
Add 10 μl MTS[2] or MTT[3] for 1.5 to 2 hours and read on Multiscanner (wavelengths 492/690)

[1] Additives for culture of LIM cell lines: 10 μM thioglycerol, 0.025 U/ml insulin, 1 μg/ml hydrocortisone. [2] 3-(4,5-dimethylthiazol-2-yl)-5-(3-carboxymethoxyphenyl)-2-(4-sulfo phenyl)-2H-tetrazolium. [3] 3-(4,5-Dimethylthiazol-2-yl)-2,5-diphenyltetrazolium bromide

Example 2.6.2

Cell Lines Used in MTS Assay

LIM2537 human colon carcinoma cell line, grown in RPMI+Adds[1]+5% FCS

Example 2.6.3

Cell Plating: One Cell Line Per Plate

Cells are trypsinized and washed ×2 in medium+5% FCS and plate out at $10^4$ cells per well in 100 μl.
Incubate plates o/n 37° C.+5%-10% CO2 incubator.

Example 2.6.4

Inhibitors

Inhibitors are dissolved in DMSO to make 10 mM stocks and titrated in a 96 well plate in duplicate to use as the stock for the test plate. Titration range from 40 μM down to 0.01 μM in ½ dilutions and 100 μl of each dilution transferred to the appropriate wells of the test plate that contains the cells (also in 100 μl) which results in the final concentration of the inhibitors being 20 μM down to 0.01 μM across the rows in duplicate. Three inhibitors are tested per plate (Rows A-F).
Each plate has the following:
Rows A,B: Inhibitor 1 dilutions, 200 μl per well
Rows C,D: Inhibitor 2 dilutions, 200 μl per well
Rows E,F: Inhibitor 3 dilutions, 200 μl per well
Control row G1-6: Medium+5% FCS (for maximum growth)
Control row G7-12: Taxol (250 nM for maximal inhibition)
Control row H: Remove medium from cells and replace with 200 μl Serum Free medium for serum free growth rate.

Example 2.6.5

Incubation

Incubate plates for 4 days in incubator. Process with MTS or MTT as outlined below.

Example 2.6.6

MTS Assay

To each well add 10 μl MTS (Sigma) solution. Incubate MTS for 1.5 to 2 hours and MTT for 4 hours. Stop reaction by adding 10 μl 10% SDS to each well. Read on Multiscan (492/690) plate reader, plot colour change versus concentration of inhibitor to establish the $IC_{50}$.

Example 2.6.7

MTT Assay

MTT Solution
MTT (Sigma M-2128)—5 g dissolved in PBS, at 5 mg/ml, filter sterilized and stored at −20° C. Thaw when required.
MTT Solvent (acidified isopropanol)
a. 1M HCl: Mix 44.6 ml conc HCl (11.2M) in 500 ml DDW
b. Acidified isopropanol (Isopropanol with 0.04N HCl): Mix 20 ml M HCl with 480 ml isopropanol (Propan-2-ol, iso-Propyl Alcohol)
MTT Addition
Add 10 μl MTT solution to each well and incubate for 4 hrs in 37° C. incubator.
Spin plates, 5 min at 1500 rpm and carefully flick out medium, without disturbing the resultant crystals. Add 200 μl acidified isopropanol (MTT Solvent) per well.
Place on plate shaker, RT, speed 6.5, for 10 min-30 min.
Read OD of plates on Thermo Multiskan Ex, at 560/690 nm.

Example 2.6.8

Results of MTS Assay on Selected Compounds of the Present Invention Using LIM2537 Human Colon Carcinoma Cell Line

TABLE 4

Results of MTS Assay on selected compounds of the present invention using LIM2537 human colon carcinoma cell line

| Compound Number | $IC_{50}$ Range (μM) |
|---|---|
| 13 | >0.1-1 |
| 14 | >10 |
| 15 | 1-10 |
| 16 | ≤0.1 |
| 17 | ≤0.1 |
| 18 | >0.1-1 |
| 19 | >0.1-1 |
| 20 | >0.1-1 |
| 21 | 1-10 |
| 22 | >10 |
| 23 | 1-10 |
| 24 | >0.1-1 |

The invention claimed is:
1. A compound of Formula III or a pharmaceutically acceptable derivative, hydrate or salt thereof, wherein:

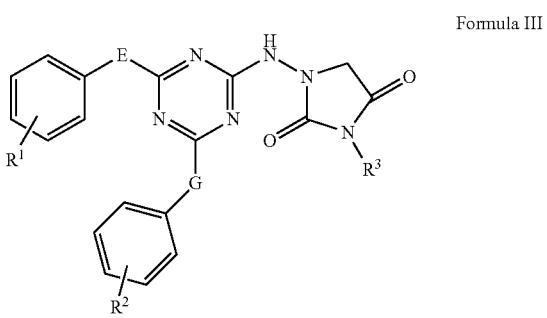

Formula III

E and G are each independently selected from the group consisting of $C_{1-4}$alkyl, —NH—, —O— and, in either orientation, —NH—$C_{1-4}$alkyl-, and —O—$C_{1-4}$alkyl-;

$R^1$ is 0-2 substituents wherein each substituent is independently selected from the group consisting of —$C_{1-4}$alkyl, —$C_{3-6}$cycloalkyl, —OH, —O—$C_{1-4}$ alkyl, —N($R^4$)$_2$, —$C_{1-4}$alkylNHR$^4$, —O—$C_{1-4}$ alkyl-N($R^4$)$_2$, —$C_{3-6}$cycloalkyl-N($R^4$)$_2$, —O-phenyl, —O-benzyl, —NO$_2$, halogen, and CF$_3$;

wherein each $R^4$ is independently selected from the group consisting of —H, —OH, $C_{1-4}$alkyl, —C(O)OC$_{1-4}$alkyl, —$C_{1-4}$alkyl-OR$^7$, and —C(O)R$^5$, provided that if one $R^4$ is OH then the other $R^4$ cannot be OH; or —N($R^4$)$_2$ forms a pyrrolidinyl, piperidinyl, piperazinyl, or morpholino group optionally substituted with $C_{1-4}$ alkyl;

$R^2$ is 0-2 substituents wherein each substituent is independently selected from the group consisting of —$C_{1-4}$alkyl, —$C_{3-6}$cycloalkyl, —OH, —O—$C_{1-4}$ alkyl, —N($R^6$)$_2$, —$C_{1-4}$ alkylN($R^6$)$_2$, —O—$C_{1-4}$alkyl-N($R^6$)$_2$, —$C_{3-6}$cycloalkyl-N($R^6$)$_2$, —O-phenyl, —O-benzyl, —NO$_2$, halogen, and CF$_3$;

each $R^6$ is independently selected from the group consisting of —H, —OH, —$C_{1-4}$alkyl, —C(O)OC$_{1-4}$alkyl, —$C_{1-4}$alkyl-OR$^7$, and —C(O)R$^8$, provided that if one $R^6$ is OH then the other $R^6$ cannot be OH; or —N($R^6$)$_2$ forms a pyrrolidinyl, piperidinyl, piperazinyl, or morpholino group optionally substituted with $C_{1-4}$alkyl;

wherein each of $R^5$ and $R^8$ are independently selected from the group consisting of —$C_{1-4}$alkyl and phenyl;

$R^3$ is selected from the group consisting of H, $C_{1-4}$alkyl, and aryl;

wherein $R^7$ is selected from the group consisting of —H and —$C_{1-4}$alkyl; and wherein the derivative has one or more quarternised basic nitrogen-containing groups or one or more esterified hydroxyl groups.

2. A compound according to claim 1 wherein each of E and G are both independently selected from —NHC$_{1-4}$alkyl.

3. A compound according to claim 2 wherein the heteroatoms of E and G are both bonded to the triazine ring.

4. A compound according to claims 1 wherein $R^1$ and $R^2$ are each independently 1-2 substituents.

5. A compound according to claim 1, wherein each of $R^1$ and $R^2$ is at least one para substituent.

6. A compound according to claim 1, wherein each $R^1$ substituent is independently selected from the group consisting of —OH, —O—$C_{1-4}$alkyl, and —$C_{1-4}$alkyl.

7. A compound according to claim 1, wherein each $R^2$ substituent is independently selected from the group consisting of —OH, O—$C_{1-4}$alkyl, and —$C_{1-4}$alkylN($R^6$)$_2$.

8. A compound according to claim 1, wherein $R^3$ is selected from the group consisting of H, methyl, propyl, butyl and phenyl.

9. A compound according to claim 1, wherein $R^3$ is hydrogen.

10. A compound according to claim 1, or a pharmaceutically acceptable derivative, hydrate or salt thereof, selected from the group consisting of:

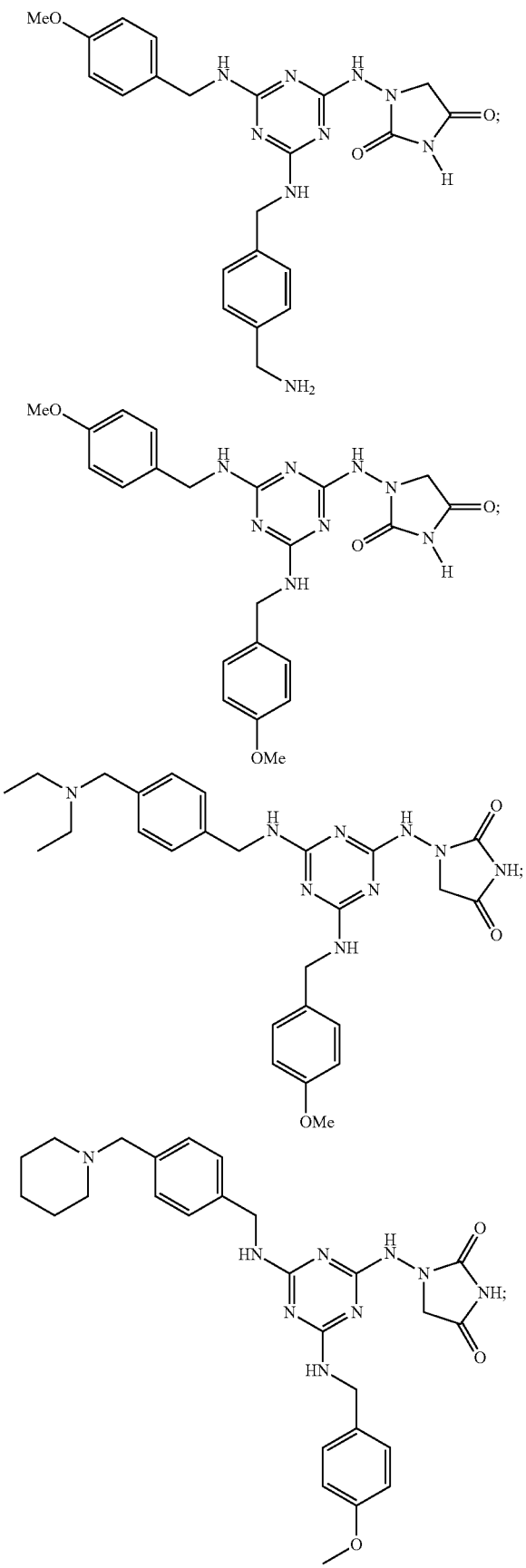

57
-continued

58
-continued

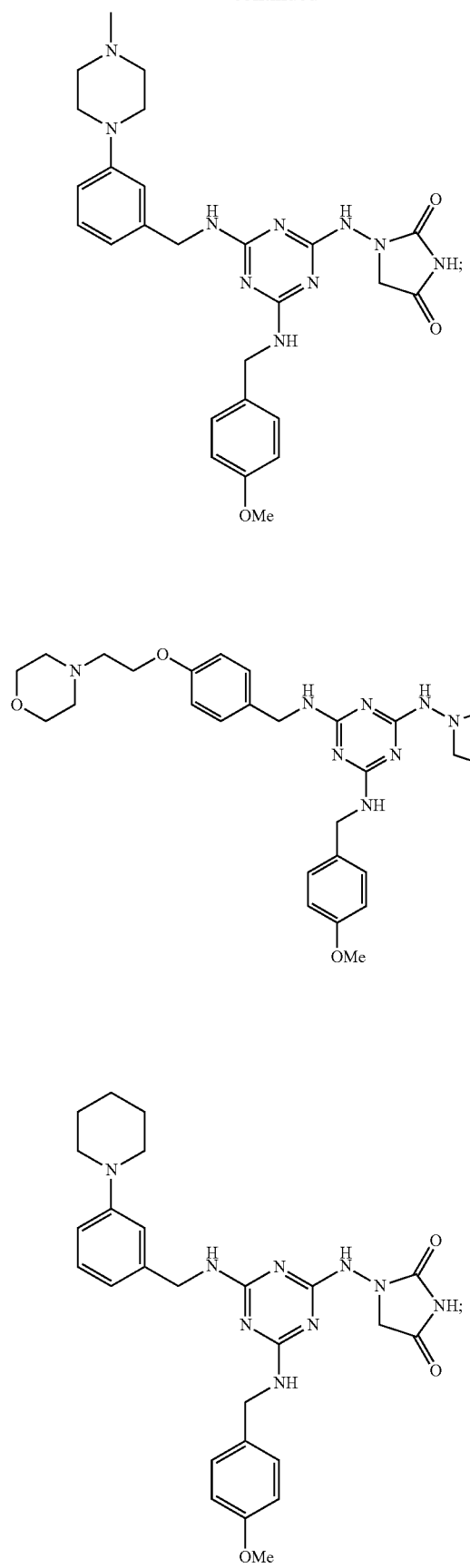
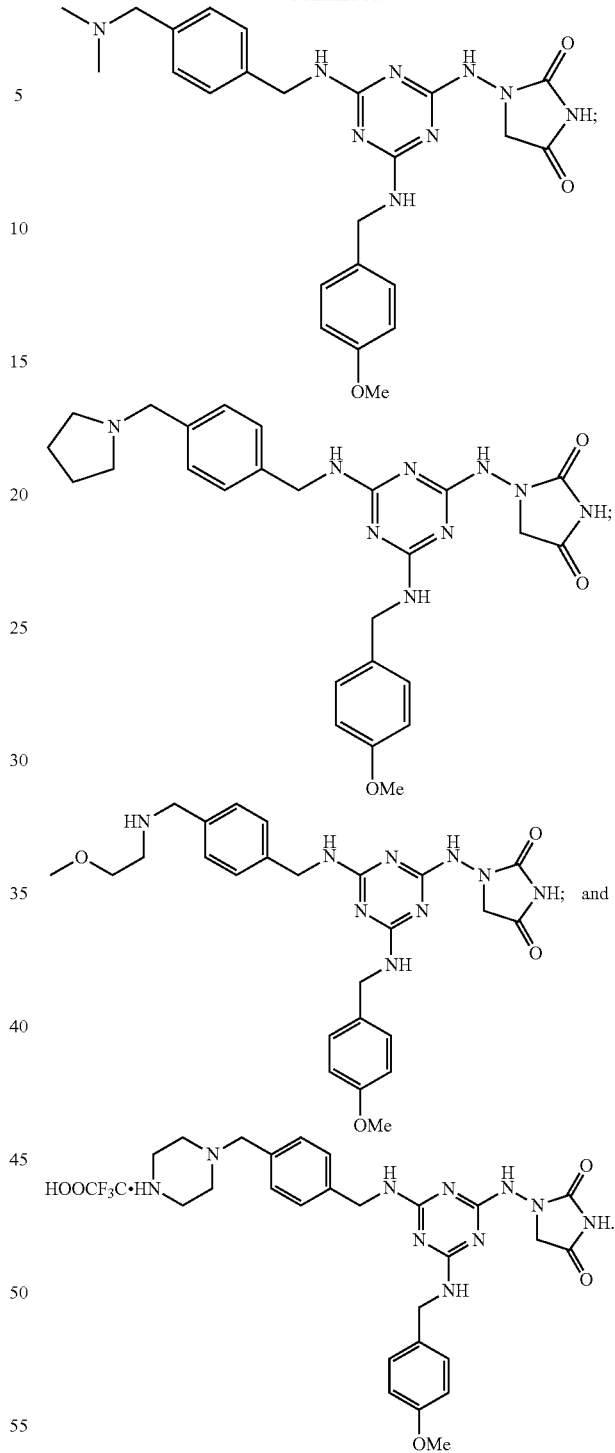

11. A method of treatment of cancer in a subject comprising administering to said subject an effective amount of a compound according to claim 1 or a pharmaceutically acceptable derivative, hydrate or salt thereof, wherein the cancer is colon cancer, non-small cell lung cancer, brain cancer or breast cancer.

12. A pharmaceutical composition comprising a compound according to claim 1, or pharmaceutically acceptable derivative, hydrate or salt thereof, and a pharmaceutically acceptable carrier, diluent or excipient.

13. A compound according to claim 1, wherein the pharmaceutically acceptable salt is a hydrochloride salt.

14. A method for inhibiting cancer cell replication or reducing tumor size in a subject, comprising exposing cancer cells or a tumor in the subject, in vivo, with an effective amount of a compound according to claim 1 or a pharmaceutically acceptable derivative, hydrate or salt thereof, wherein the cancer is colon cancer, non-small cell lung cancer, brain cancer or breast cancer.

15. The method according to claim 14, wherein the cancer is resistant to treatment with a taxane.

16. The method according to claim 11, wherein the cancer is resistant to treatment with a taxane.

\* \* \* \* \*